United States Patent
Pestotnik et al.

(10) Patent No.: US 7,213,009 B2
(45) Date of Patent: May 1, 2007

(54) SYSTEMS AND METHODS FOR MANIPULATING MEDICAL DATA VIA A DECISION SUPPORT SYSTEM

(75) Inventors: Stanley L. Pestotnik, Sandy, UT (US); Jonathan B. Olson, Salt Lake City, UT (US); Matthew H. Samore, Salt Lake City, UT (US); R. Scott Evans, North Salt Lake, UT (US); Barry M. Stults, Salt Lake City, UT (US); Michael A. Rubin, Salt Lake City, UT (US); William H. Tettelbach, Salt Lake City, UT (US); William F. Harty, III, Salt Lake City, UT (US); Richard J. Boekweg, Tooele, UT (US); Bo Lu, Salt Lake City, UT (US); David D. Eardley, Salt Lake City, UT (US); Michael E. Baza, West Bountiful, UT (US); Mark H. Skolnick, Salt Lake City, UT (US); Merle A. Sande, Salt Lake City, UT (US)

(73) Assignee: Theradoc, Inc., Salt Lake City, UT (US)

( * ) Notice: Subject to any disclaimer, the term of this patent is extended or adjusted under 35 U.S.C. 154(b) by 314 days.

(21) Appl. No.: 10/658,998

(22) Filed: Sep. 9, 2003

(65) Prior Publication Data

US 2004/0260666 A1 Dec. 23, 2004

Related U.S. Application Data

(62) Division of application No. 09/666,429, filed on Sep. 21, 2000, now abandoned.

(51) Int. Cl.
G06N 5/00 (2006.01)

(52) U.S. Cl. .......................... 706/46; 706/45

(58) Field of Classification Search ................ 706/46; 434/363; 600/483
See application file for complete search history.

(56) References Cited

U.S. PATENT DOCUMENTS

| | | | | |
|---|---|---|---|---|
| 4,290,114 A | | 9/1981 | Sinay | 364/900 |
| 4,428,733 A | * | 1/1984 | Kumar-Misir | 434/363 |
| 4,595,982 A | * | 6/1986 | Burt | 706/46 |
| 4,839,822 A | | 6/1989 | Dormond et al. | 364/513 |
| 4,982,738 A | * | 1/1991 | Griebel | 600/483 |

(Continued)

OTHER PUBLICATIONS

"HELP's Pharmacy System," *I/O; An Update from IHC-NET*, vol. 1, No. 4, Jul./Aug. 1989, pp. 1–2, 4.*

(Continued)

*Primary Examiner*—Wilbert Starks, Jr.
(74) *Attorney, Agent, or Firm*—Workman Nydegger

(57) ABSTRACT

Disclosed is a method for delivering decision-supported patient data to a clinician to aid the clinician with the diagnosis and treatment of a medical condition. The method including presenting a patient with questions generated by a decision-support module and gathering patient data indicative of the responses to the questions. Each question presented to the patient is based upon the prior questions presented to and the patient data gathered from the patient. Upon receiving the patient data from the client module, evaluating the patient data at the module to generate decision-supported patient data, this supported patient data includes medical condition diagnoses, pertinent medical parameters for the medical condition, and medical care recommendations for the medical condition. At the client module or a clinician's client module, presenting the clinician with this patient data in either a standardized format associated with a progress note or a format selected by the clinician.

36 Claims, 31 Drawing Sheets

U.S. PATENT DOCUMENTS

| | | | | |
|---|---|---|---|---|
| 5,018,067 | A | 5/1991 | Mohlenbrock et al. | 364/413.02 |
| 5,255,187 | A | 10/1993 | Sorensen | 364/413.02 |
| 5,301,105 | A | 4/1994 | Cummings, Jr. | 364/401 |
| 5,473,537 | A | 12/1995 | Glazer et al. | 364/419.2 |
| 5,517,405 | A | 5/1996 | McAndrew et al. | 364/401 |
| 5,551,436 | A | 9/1996 | Yago | 128/670 |
| 5,583,758 | A | 12/1996 | McIlroy et al. | 395/202 |
| 5,737,539 | A | 4/1998 | Edelson et al. | 395/203 |
| 5,764,923 | A | 6/1998 | Tallman et al. | 395/203 |
| 5,833,599 | A | 11/1998 | Schrier et al. | 600/300 |
| 5,839,438 | A | 11/1998 | Graettinger et al. | 600/300 |
| 5,845,255 | A | 12/1998 | Mayaud | 705/3 |
| 5,908,383 | A | 6/1999 | Brynjestad | 600/300 |
| 6,009,420 | A | 12/1999 | Fagg, III et al. | 706/45 |
| 6,029,138 | A | 2/2000 | Khorasani et al. | 705/2 |
| 6,049,794 | A | 4/2000 | Jacobs et al. | 706/45 |
| 6,188,988 | B1 | 2/2001 | Barry et al. | 705/3 |
| 6,234,964 | B1 | 5/2001 | Iliff | 600/300 |
| 6,247,004 | B1 | 6/2001 | Moukheibir | 706/46 |
| 6,260,022 | B1 * | 7/2001 | Brown | 705/2 |
| 6,272,481 | B1 | 8/2001 | Lawrence et al. | 706/45 |
| 6,317,719 | B1 | 11/2001 | Schrier et al. | 705/2 |
| 6,334,778 | B1 * | 1/2002 | Brown | 434/262 |
| 6,443,889 | B1 | 9/2002 | Groth et al. | 600/300 |
| 6,482,156 | B2 | 11/2002 | Iliff | 600/300 |
| 2001/0050610 | A1 | 12/2001 | Gelston | 340/5.53 |
| 2002/0002472 | A1 | 1/2002 | Abraham-Fuchs | 705/3 |
| 2002/0002473 | A1 | 1/2002 | Schrier et al. | 705/3 |
| 2002/0040282 | A1 | 4/2002 | Bailey et al. | 702/188 |
| 2002/0080189 | A1 | 6/2002 | Dvorak et al. | 345/810 |
| 2002/0083075 | A1 | 6/2002 | Brummel et al. | 707/102 |
| 2002/0091687 | A1 | 7/2002 | Eglington | 707/5 |
| 2002/0099273 | A1 | 7/2002 | Bocionek et al. | 600/300 |
| 2002/0107824 | A1 | 8/2002 | Ahmed | 706/46 |
| 2002/0116222 | A1 | 8/2002 | Wurster | 705/2 |
| 2002/0143262 | A1 | 10/2002 | Bardy | 600/508 |
| 2002/0178031 | A1 | 11/2002 | Sorensen | 705/2 |
| 2004/0260666 | A1 | 12/2004 | Pestotnik et al. | 706/46 |

OTHER PUBLICATIONS

Bleigh, Howard L., M.D., "The Computer as a Consultant," *Seminars in Medicine of the Beth Israel Hospital, Boston*, vol. 284, No. 3, Jan. 21, 1971, pp. 141–147.*

Bleigh, Howard L., M.D., et al., "Clinical Computing in a Teaching Hospital," *The New England Journal of Medicine*, vol. 312, No. 12, Mar. 21, 1985, pp. 756–764.*

Bradshaw, Karen E., et al., "Development of a Computerized Laboratory Alerting System," *Computers and Biomedical Research*, vol. 22, 1989, pp. 575–587.*

Gardner, Reed M., Ph.D., "Computerized Data Management and Decision Making in Critical Care," *Surgical Clinics of North America*, vol. 65, No. 4, Aug. 1985, pp. 1041–1051.*

McDonald, Clement J., M.D., et al., "The Regenstrief Medical Records," *M.D. Computing*, vol. 5, No. 5, 1988, pp. 34–47.*

Stead, William W., M.D., et al., "Computer–Based Medical Records: The Centerpiece of TMR," *M.D. Computing*, vol. 5, No. 5, 1988, pp. 48–61.*

Yu, Victor L., M.D., et al., "Antimicrobial Selection by a Computer—A Blinded Evaluation by Infectious Experts," *JAMA*, vol. 242, No. 12, Sep. 21, 1979, pp. 1279–1282.*

Plaintiff Allcare's Claim Chart Amendments in Response to Stipulated Order Regarding Same, Jun. 27, 2000, 14 pgs.

Alpay, L., et al., "Model–Based Application: The Galen Structured Clinical User Interface," pp. 307–318.

Arkad, K., et al., "Medical Logic Module (MLM) representation of knowledge in a ventilator treatment advisory system," *International Journal of Clinical Monitoring and Computing*, 1991, pp. 43–48.

Armstrong, Carl W., "AHA Guide to Computerized Physician Order–Entry Systems," American Hospital Association, Nov. 2000, pp. 1–48.

Astion, Michael L., et al., "Application of Neural Networks to the Classification of Giant Cell Arteritis," *Arthritis & Rheumatism*, vol. 37, No. 5, May 1994, pp. 760–770.

Astion, Michael L., et al., "Neural Networks as Expert Systems in Rheumatic Disease Diagnosis: Artificial Intelligence Artifice?" *The Journal of Rheumatology*, 1993, vol. 20, No. 9, pp. 1465–1468.

Austin, Tony et al., "A Prototype Computer Decision Support System for the Management of Asthma," *Journal of Medical Systems*, vol. 20, No. 1, 1996, pp. 45–55.

Aydin, Carolyn E., et al., "Transforming Information Use in Preventive Medicine: Learning to Balance Technology with the Art of Caring," pp. 563–567, available on information and belief at least as early as 1994.

Balas, E. Andrew et al.,"Improving Preventive Care by Prompting Physicians," *Arch Intern Med*, vol. 160, Feb. 14, 2000, pp. 301–308.

Balas, E. Andrew et al., "The Clinical Value of Computerized Information Services—A Review of 98 Randomized Clinical Trials," *Arch Fam Med*, vol. 5, May 1996, pp. 271–278.

Bates, David W., "Using information technology to reduce rates of medication errors in hospitals," *BMJ*, vol. 320, Mar. 18, 2000, pp. 788–791.

Bates, David W., et al., "The Impact of Computerized Physician Order Entry on Medication Error Prevention," *Journal of the American Medical Informatics Association*, Jul./Aug. 1999, vol. 6, No. 4, pp. 313–321.

Berger, Jeffrey, "Roentgen: Radiation Therapy and Case–based Reasoning," pp. 171–177.

Bernstein, Robert M., et al., "Prompting Physicians For Cost–Effective Test Ordering in The Low Prevalence Conditions of Family Medicine," pp. 824–828, available on information and belief at least as early as 1994.

Bichindaritz, Isabelle, "A Case–Based Assistant for Clinical Psychiatry Expertise," pp. 673–677.

Brickley, Mark R., et al., "Performance of a Neural Network Trained to Make Third–molar Treatment–planning Decisions," pp. 153–160, available on information and belief at least as early as 1994.

Burke, J.P., et al., "Computer–Assisted Prescribing and its Impact on Resistance," *Antibiotic therapy and control of antimicrobial resistance in hosptials*, pp. 89–95, available on information and belief at least as early as 1999.

Burke, J.P., et al., "Antibiotic Use and Microbial Resistance in Intensive Care Units: Impact of Computer–Assisted Decision Support," *Journal of Chemotherapy*, vol. 11, No. 6, 1999, pp. 530–535.

Carenini, Giuseppe et al., "An Information–Based Bayesian Approach to History Taking," pp. 129–138.

Carson, E.R., et al., "Evaluating Intelligent Measurement Systems: A Study in Ventilator Management," *IEEE Engineering in Medicine & Biology Society 11th Annual International Conference* pp. 1769–1770, available on information and belief at least as early as 1989.

Casanova, Andrea et al., "Reasoning with Cases in Clinical Problem Solving," pp. 1986–1990, available on information and belief at least as early as 1995.

Chambrin, Marie–Christine et al., "RESPAID: Computer Aided Decision Support for Respiratory Data in I.C.U.," *IEEE Engineering in Medicine & Biology Society 11th Annual International Conference*, pp. 1776–1777, available on information and belief at least as early as 1989.

Cheung, John Y., et al., "Detection of Abnormal Electrocardiograms Using a Neural Network Appraoch," *IEEE Engineering in Medicine & Biology Society 11th Annual International Conference*, pp. 2015–2016, available on information an belief at least as early as 1989.

Classen, David C., et al., "Description of a Computerized Adverse Drug Event Monitor Using a Hospital Information System," *Hospital Pharmacy*, vol. 27, Sep. 1992, pp. 774, 776–779, 783.

Darmoni, Stéfan J., et al., "Functional Evaluation of Seth: An Expert System in Clinical Toxicology," pp. 231–238, available on information and belief at least as early as 1994.

Davis, Randall et al., "Retrospective on 'Production rules as a representation for a knowledge–based consultation program,'" *Artificial Intelligence 59* (1993), pp. 181–189.

DeJesus, Edmond X., "Achieving Expert Ease," *Healthcare Informatics: Achieving Expert Ease*, Jan. 2000, pp. 1–10.

Do Amaral, M.B., et al., "A Psychiatric Diagnostic System Integrating Probabilistic and Categorical Reasoning," *Methods of Information in Medicine*, 1995, vol. 34, No. 3, pp. 232–243.

Dojat, Michel et al., "Evaluation of a Knowledge–based System Providing Ventilatory Management and Decision for Extubation," *American Journal of Respiratory and Critical Care Medicine*, vol. 153, 1996, pp. 997–1004.

Downs, Joseph et al., "A Prototype Neural Network Decision–Support Tool for the Early Diagnosis of Acute Myocardial Infarction," pp. 355–366.

Doyle, H.R., et al., "Building Clinical Classifiers Using Incomplete Observations—A Neural Network Ensemble for Hepatoma Detection in Patients with Cirrhosis," *Methods of Information in Medicine*, 1995, 6 pages.

Ebell, Mark H., "Artificial Neural Networks for Predicting Failure to Survive Following In–Hospital Cardiopulmonary Resuscitation," *The Journal of Family Practice*, vol. 36, No. 3, pp. 297–303, 1993.

Eccles, Martin et al., "Effect of computerised evidence based guidelines on management of asthma and angina in adults in primary care: cluster randomised controlled trial," *BMJ*, vol. 325, Oct. 26, 2002, pp. 1–7.

Evans, Carl D., et al., "A Case–Based Learning Approach to Grouping Cases with Multiple Malformations," *MD Computing*, 1995, vol. 12, No. 2, pp. 127–136.

Evans, R. Scott et al., "Improving Empiric Antibiotic Selection Using Computer Decision Support," *Archives of Internal Medicine*, vol. 154, Apr. 25, 1994, pp. 878–884.

Evans, R. Scott et al., "Reducing the Duration of Prophylactic Antibiotic Use Through Computer Monitoring of Surgical Patients," *DICP, The Annals of Pharmacotherapy*, Apr. 1990, vol. 24, pp. 351–354.

Evans, R. Scott et al., "Preventing Adverse Drug Events In Hospitalized Patients," *The Annals of Pharmacotherapy*, vol. 28, Apr. 1994, pp. 523–527.

Evans, R. Scott et al., "Evaluation of a Computer–Assisted Antibiotic–Dose Monitor," *The Annals of Pharmacotherapy*, vol. 33, Oct. 1999, pp. 1026–1031.

Evans, R. Scott et al., "Development Of An Automatic Antibiotic Consultant," *M.D. Computing*, vol. 10, No. 1, 1993, pp. 17–22.

Evans, R. Scott et al., "A Computer–Assisted Management Program For Antibiotics and other Antiinfective Agents," *The New England Journal of Medicine*, vol. 338, No. 4, Jan. 22, 1998, pp. 232–239.

Evans, R. Scott, et al., "Prevention of Adverse Drug Events through Computerized Surveillance," pp. 437–441.

Evans, R. Scott, et al., "A Decision Support Tool for Antibiotic Therapy," pp. 651–655.

Evans, R. Scott, "Development of a Computerized Infectious Disease Monitor (CIDM)," *Computers and Biomedical Research*, vol. 18, 1985, pp. 103–113.

Fiocchi, R et al., "A Neural Support to the Prognostic Evaluation of Cardiac Surgery," pp. 435–436.

Goldberg, Dean E., et al., "Computer–based Program For Indentifying Medication Orders Requiring Dosage Modification Based On Renal Function," *AJHP*, vol. 48, Sep. 1991, pp. 1965–1969.

Grimson, Jane B, "Integrating Knowledge–based Systems and Databases," *Clinica Chimica Acta*, 1993, vol. 222, pp. 101–115.

Grossi, Eugene A., et al., "Use of Arificial Intelligence to analyze clinical database reduces workload on surgical house staff,"*Surgery*, vol. 116, No. 2, pp. 250–254, Aug. 1994.

Habbema, "Chapter 18: Predictive Tools for Clinical Decision Support," Handbook of our Medical Informatics, pp. 292–305.

Hamamoto, Isao et al., "Prediction of the Early Prognosis of the Hepatectomized Patient with Hepatocellular Carcinoma with a Neural Network," *Computer Bio Med.*, vol. 25, No. 1, 1995, pp. 49–59.

Hammond, Peter, "OaSiS: Integrating safety reasoning for decision support in oncology," pp. 185–191.

Harber, Philip et al., "An Expert System Based Preventive Medicine Examination Adviser," *JOEM*, vol. 37, No. 5, May 1995, pp. 563–570.

Henry, Suzanne Bakken et al., "A Template–based Approach to Support Utilization of Clinical Practice Guidelines Within an Electronic Health Record," *Journal of the American Medical Informatics Association*, vol. 5, No. 3, May/Jun. 1998, pp. 237–244.

Heras, J., et al., "TKR–tool: An Expert System for Total Knee Replacement Management," pp. 444–446, available on information an belief at least as early as 1994.

Hripcsak, George et al., "The Columbia–Presbyterian Medical Center Decision–Support System as a Model for Implementing the Arden Syntax," *Proceedings of the Annual Symposium on Computer Applications in Medical Care*, 1991, pp. 248–252.

Hunt, Dereck et al., "Effects of Computer–Based Clinical Decision Support Systems on Physician Performance & Patient Outcomes," *JAMA*, vol. 280, No. 15, Oct. 21, 1998, pp. 1339–1346.

James, Brent C., et al., "Making It Easy To Do It Right," *The New England Journal of Medicine*, vol. 345, No. 13, Sep. 27, 2001, pp. 991–993.

Johansson, Bo et al., "Arden Syntax As A Standard For Knowledge Bases In The Clinical Chemistry Laboratory," Clinica Chimica Acta 222, 1993, pp. 123–128.

Johnston, Mary E., et al., "Effects of Computer–based Clinical Decision Support Systems on Clinician Performance and Patient Outcome—A Critical Appraisal of Research," *Annals of Internal Medicine*, vol. 120, No. 2, Jan. 15, 1994, pp. 135–142.

Kahan, B.D., "Frontiers For the Coming Millennium," *Transplantation Proceedings*, vol. 28, No. 4, (Aug.) 1996, pp. 2299–2306.

Kahn, Charles E, Jr., "Artificial Intelligence in Radiology: Decision Support Systems," *RadioGraphics*, Jul. 1994, vol. 14, No. 4, pp. 849–861.

Kahn, Charles E, Jr., et al., "Case–based Reasoning and Imaging Procedure Selection," *Investigative Radiology*, vol. 29, No. 6, Jun. 1994, pp. 643–647.

Kahn, Charles E., Jr., "Planning Diagnostic Imaging Work–up Strategies using Case–Based Reasoning," pp. 931–935.

Kanoui, Henry et al., "A Knowledge–Based Modeling Hospital Information Systems Components," pp. 319–330.

Ketcherside, W. Joseph et al., "Prediction of Survival In Trauma Patients using Probabilistic Neural Networks," 4 pages.

Ketikidis, P.H., et al., "Arres: Computer Assisted Post Anesthesia Care Unit Monitoring System," *IEEE Engineering in Medicine & Biology Society 11$^{th}$ Annual International Conference*, pp. 1855–1856, available on information and belief at least as early as 1989.

Kindler H., et al., "An Advisor for the Management of the Acute Radiation Syndrome," pp. 386–396.

Kuperman, Gilad J., et al., "Detecting Alerts, Notifying the Physician, and Offering Action Items: A Comprehensive Alerting System," pp. 704–708, available on information and belief at least as early as 1996.

Kuperman, Gilad J., et al., HELP: A Dynamic Hospital Information System, 1991, Springer–Verlag New York Inc., ISBN 0–387–97431–8, pp. 1–13, 34–52.

Kuperman, Gilad J., et al., "Representing Hospital Events as Complex Conditionals," pp. 137–141, available on information and belief at least as early as 1995.

Larsen, Robert A., et al., "Improved Perioperative Antibiotic Use and Reduced Surgical Wound Infections Through use of Computer Decision Analysis," *Infect Control Hospital Epidemiol*, vol. 10, No. 7, 1989, pp. 316–320.

Leão, Beatriz De F., et al., "Hycones: A Hybrid Approach to Designing Decision Support Systems," *MD Computing*, vol. 13, No. 2, 1996, pp. 160–164.

Lee, Susan Ciarrocca, "Using a Translation–Invariant Neural Network to Diagnose Heart Arrhythmia," *IEEE Engineering in Medicine & Biology Society 11$^{th}$ Annual International Conference*, pp. 2025–2026, available on information and belief at least as early as 1989.

Lehmann, E.D., et al., "Combining Rule–based reasoning and mathematical modelling in diabetes care," Artificial Intelligence in Medicine 6 (1994), pp. 137–160.

Lette, Jean et al., "Artificial Intelligence Versus Logistic Regression Statistical Modelling to Predict Cardiac Complications after Noncardiac Surgery," *Clin. Cardiol*, vol. 17, Nov. 1994, pp. 609–614.

Li, Yu–Chuan, et al., "Assessing the Behavioral Impact of a Diagnostic Decision Support System," 1995, pp. 805–809.

Lin, Kang–Ping, et al., "Classification of QRS Pattern by an Associative Memory Model" *IEEE Engineering in Medicine & Biology Society 11$^{th}$ Annual International Conference*, pp. 2017–2018, available on information and belief at least as early as 1989.

Maceratini, R., et al., "Expert Systems and the Pancreatic Cancer Problem: decision support in the pre–operative diagnosis," *J. Biomed. Eng.*, Nov. 1989, vol. 11, pp. 487–510.

Maclin, Phillip S., et al., "How to Improve a Neural Network for Early Detection of Hepatic Cancer," *Cancer Letters*, vol. 77, 1994, pp. 95–101.

Mann, N. Horace, III, et al., "Artificial Intelligence in the Diagnosis of Low Back Pain," *Orthopedic Clinics of North America*, vol. 22, No. 2, Apr. 1991, pp. 303–314.

Matisoff, Marty, "Cybernetics, Artificial Neural Networks & Medicine," *Journal of Clinical Engineering* vol. 20, No. 6, Nov./Dec. 1995, 7 pages.

McCauley, Nancy, et al., "The Use of Expert Systems in the Healthcare Industry," *Information & Management*, vol. 22., 1992, pp. 227–235.

McDonald, Clement J., et al., "The Promise of Computerized Feedback Systems for Diabetes Care," *Ann Intern Med*, vol. 124, 1996, pp. 170–174.

Metzger, Jane, et al., "Clinical Decision Support for the Independent Physician Practice," *ihealthreports*, California HealthCare Foundation, First Counseling Group, Oct. 2002, pp. 1–41.

Molino, G., et al., "Design of a Computer–assisted Programme Supporting The Selection and Clinical Management of Patients Referred for Liver Transplantation," *Ital J Gastroenterol*, vol. 26, 1994, pp. 31–43.

Monane, Mark, et al., "Improving Prescribing Patterns for the Elderly Through an Online Drug Utilization Review Intervention: A System Linking the Physician, Pharmacist, and Computer," *JAMA*, vol. 280, No. 14, Oct. 14, 1998, pp. 1249–1252.

Musen, Mark A., et al., "A Component–Based Architecture for Automation of Protocol–Directed Therapy," pp. 3–13.

Musen, Mark A., et al., "Medical Informatics: Computer Applications in Health Care and Biomedicine," Chapter 16: Clinical Decision –Support Systems, pp. 572–609.

Musen, Mark A., et al., "A Rational Reconstruction of INTERNIST–I using PROTÉGÉ–II," pp. 289–293, available on information and belief at least as early as 1995.

Pestotnik, Stanley L., et al., "Implementing Antibiotic Practice Guidelines through Computer–Assisted Decision Support: Clinical and Financial Outcomes," *Annals of Internal Medicine*, vol. 124, No. 10, May 15, 1996, pp. 884–890.

Pestotnik, Stanley L., et al., "Prospective Surveillance of Imipenem/Cilastatin Use and Associated Seizures Using a Hospital Information System," *The Annals of Pharmacotherapy*, vol. 27, Apr. 1993, pp. 497–501.

Pestotnik, Stanley L., et al., "Therapeutic Antibiotic Monitoring: Surveillance Using a Computerized Expert System," *The American Journal of Medicine*, vol. 88, Jan. 1990, pp. 43–48.

Pietka, Ewa, "Neutal Nets for ECG Classification," *IEEE Engineering in Medicine & Biology Society 11$^{th}$ Annual International Conference*, pp. 2021–2022, available on information and belief at least as early as 1989.

Pryor, T. Allan, et al., "Sharing MLM's: An Experiment Between Clomubia–Presbyterian and LDS Hospital," *Proceedings –The Annual Symposium on Computer Applications in Medical Care*, pp. 399–403, available on information and belief at least as early as 1994.

Pryor, T. Allan, "The Help Medical Record System," *M.D. Computing*, 1988, vol. 5, No. 5, pp. 22–33.

Pryor, T. A., et al., "The HELP System," Journal of Medical Systems, vol. 7, No. 2, 1983, pp. 87–102.

Raschke, Robert A., et al., "A Computer Alert System to Prevent Injury From Adverse Drug Events: Developmental and Evaluation in a Community Teaching Hospital," *JAMA*, vol. 280, No. 15, Oct. 21, 1998, pp. 1317–1320.

Rector, Al, et al., "Shedding Light on Patients' Problems: Integrating Knowledge Based Systems Into Medical Practice," pp. 531–534.

Sabbatini, Renato M. E., "Using Neural Networks for Processing Biologic Signals," *Computing in Brazil*, pp. 152–159.

Safran, Charles, et al., "Development of a Knowledge–based Electronic Patient Record," *MD Computing*, vol. 13, No.1, 1996, pp. 46–54, 63.

Saranummi, Niilo, et al., "Knowledge–based Systems in Medicine—a Nordic Research and Development Programme," *Computer Methods and Programs in Biomedicine*, vol. 34, 1991, pp. 81–89.

Schiff, Gordon D., et al., "Computerized Prescribing: Building the Electronic Infrastructure for Better Medication Usage," *JAMA*, vol. 279, No. 13, Apr. 1, 1998, pp. 1024–1029.

Schioler, Thomas, et al., "Information Technology Factors in Transferability of Knowledge based systems in Medicine," *Artificial Intelligence in Medicine*, vol. 6, 1994, pp. 189–201.

Schloerb, Paul R., "Electronic Parenteral and Enteral Nutrition," *Journal of Parenteral and Enteral Nutrition*, Feb. 2000, vol. 24, No. 1, pp. 23–29.

Schmidt, R., et al., "Adaptation and Abstraction in a Case–based Antibiotics Therapy Adviser," pp. 209–217.

Shabot, M. Michael, et al., "Inferencing Strategies for Automated ALERTS on Critically Abnormal Laboratory and Blood Gas Data," 4 pages.

Shahar, Yuval, "Automated Support to Clinical Guidelines and Care Plans: The Intention—Oriented View," pp. 1–6.

White, Stuart C., "Decision–support Systems in Dentistry," *Journal of Dental Education*, vol. 60, No. 1, Jan. 1996, pp. 47–63.

Shortliffe, Edward H., "The Adolescence of AI in Medicine: Will the field come of age in the '90s?*," *Artificial Intelligence in Medicine*, vol. 5, 1993, pp. 93–106.

Sinnott, Margaret M., et al., "Knowledge based lipid management system for general practitioners," *Clinica Chimica Acat*, vol. 222, 1993, pp. 71–77.

Sondak, V. K., et al., "New Directions for Medical Artificial Intelligence," *Computers Math. Applic.*, vol. 20, No. 4–6, 1990, pp. 313–319.

Speight, P.M., et al., "The Use of Artificial Intelligence to Identify People at Risk of Oral Cancer and Precancer," *Br. Dental*, vol. 179, 1995, pp. 382–387.

Stefanelli, Mario, "European Research Efforts in Medical Knowledge–based Systems," *Artificial Intelligence in Medicine*, vol. 5, 1993, pp. 107–124.

Xue, Qiuzhen, et al., "A Neural Network Weight Pattern study with ECG Pattern Recognition," *IEEE Engineering in Medicine & Biology Society 11$^{th}$ Annual International Conference*, pp. 2023–2024, available on information and belief at least as early as 1989.

Szolovits, Peter, et al., "Categorical and Probabilistic Reasoning in Medicine Revisited," *Artificial Intelligence*, vol. 59, 1993, pp. 167–180.

Tang, Paul, C., et al., "ActiveGuidelines: Integrating Web–Based Guidelines with Computer–Based Patient Records," 5 pages.

Thoreux, P.H., et al., "A Microcomputer Teaching and Decision–Support System for Emergency Medicine: Use of Hypermedia and Artificial Intelligence in Combination," *Med. Inform.*, vol. 21, No. 1, 1996, pp. 35–43.

Tierney, William M., et al., "Computerizing Guidelines to Improve Care and Patient Outcomes: The Example of Heart Failure," *JAMIA*, vol. 2, No. 5, Sep./Oct. 1995, pp. 316–322.

Tong, D.A., et al., "WEANPRO: A Weaning Protocol Expert System," *IEEE Engineering In Medicine & Biology Society 11$^{th}$ Annual International Conference*, pp. 1857–1858, available on information and belief at least as early as 1989.

Torasso, Pietro, "A Report on Medical Expert Systems Research in Italy," *Artificial Intelligence in Medicine*, vol. 2, 1990, pp. 43–53.

Uckun, Serdar, "Artificial Intelligence in Medicine: State–of–the–art and Future Prospects," *Artificial Intelligence in Medicine*, vol. 5, 1993, pp. 89–91.

Van Bemmel, J.H., "Handbook of Medical Informatics," Houten/Diegem, 1997, pp. 232–260.

Van Dyne, M. M., et al., "Using Machine Learning and Expert Systems to Predict Preterm Delivery in Pregnant Women," pp. 344–350, available on information and belief at least as early as 1994.

Wagner, Michael M., et al., "Clinical Event Monitoring at the University of Pittsburgh," 6 pages.

Wang, Shengrui, et al., "An Intelligent Interactive Simulator of Clinical Reasoning in General Surgery," pp. 419–423.

Wolfram, D.A., "An Appraisal of INTERNIST–I" *Artificial Intelligence in Medicine*, vol. 7, 1995, pp. 93–116.

Zhao, Y. K., et al., "Design and Development of an Expert System to Assist Diagnosis and Treatment of Chronic Hepatitis Using Traditional Chinese Medicine", *Med. Inform.*, vol. 19, No. 1, 1994, pp. 37–45.

Burke JP, et al., "A Retrospective Analysis of Twice–daily Cefotaxime Compared to Conventional Therapy for the Treatment of Infections in a USA Hospital," *Diagn Microbial Infect Dis* 22 (1995):167–69.

Burke JP, et al., "Antibiotic Cycling: What Goes Around Comes Around," [editorial review] *Current Opinion in Infectious Diseases* 13 (2000): 367–69.

Burke JP, et al., "Antibiotic Resistance: The Combat Zone," [editorial review] *Current Opinion in Infectious Diseases* 11 (1998): 441–43.

Burke JP, et al., "Antibiotic Resistance–Systems Thinking, Chaos and Complexity Theory," [editorial review] *Current Opinion in Infectious Diseases* 12 (1999): 317–19.

Burke JP, et al., "Breaking the Chain of Antibiotic Resistance," [editorial review] *Current Opinion in Infectious Diseases* 9 (1996): 253–55.

Burke JP, et al., "The HELP System and its Application to Infection Control," *Journal of Hospital Infection* 18(Supp. A) (1991): 424–31.

Burke JP, et al., "The Quality of Antibiotic Use and the Quality of Measuring It," [editorial review] *Current Opinion in Infectious Diseases* 10 997: 289–291.

Classen DC, et al., "Adverse Drug Events in Hospitalized Patients: Excess Length of Stay, Extra Costs, and Attributable Mortality," *JAMA* 277.4 (Jan. 1997): 301–6.

Classen DC, et al., "Clinical and Financial Impact of Intravenous Erythromycin Therapy in Hospitalized Patients," *Annals of Pharmacotherapy* 33 (Jun. 1999): 669–73.

Classen DC, et al., "Computerized Surveillance of Adverse Drug Events in Hospitalized Patients," *JAMA* 266.20 (Nov. 27, 1991): 2847–51.

Classen DC, et al., "Description of a Computerized Adverse Drug Event Monitor Using a Hospital Information System," *Hospital Pharmacy* 27 (Sep. 1992):774, 776–779, 783.

Classen DC, et al., "Intensive Surveillance of Midazolam Use in Hospital Patients and the Occurrence of Cardiorespiratory Arrest," 12.3 *Pharmacotherapy* (1992): 213–16.

Classen DC, et al., "Surveillance for Quality Assessment: IV. Surveillance Using a Hospital Information Systems," 12.4 *Infection Control and Hospital Epidemiology* (Apr. 1991): 239–44.

Classen DC, et al., "The Timing of Prophylactic Adminstration of Antibiotics and the Risk of Surgical–wound Infections," *New England Journal of Medicine* 326.5 (Jan. 30, 1992): 281–86.

Evans RS et al., "A Computerized Approach to Monitor Prophylactic Antibiotics," *Proc Annu Symp Comput Appl Med Care* 11 (1987): 241–45.

Evans RS, et al., "A Decision Support Tool for Antibiotic Therapy," *Proc Annu Symp Comput Appl Med Care* 19 (1995): 651–55.

Evans RS, et al., "Applications of Medical Informatics in Antibiotics Therapy," *Antimicrobial Susceptibility Testing* 349 (1994): 87–96.

Evans RS, et al., "Computerized Identification of Patients at Risk for Hospital–Acquired Infections," *American Journal of Infection Control* 20.1 (Feb. 1992): 4–10.

Evans RS, et al., "Development of a Computerized Adverse Drug Event Monitor,", *Proc Annu Symp Comptu Appl Med Care* 15 (1991): 23–27.

Evans RS, et al., "Improving Empiric Antibiotic Selection Using Computer Decision Support," *Arch I Intern Med* 154 (Apr. 25, 1994): 878–84.

Evans RS, et al., "Prediction of Hospital Infections and Selection of Antibiotics Using an Automated Hospital Database," *Proc Annu Symp Comput Appl Med Care* 14 (1990): 663–67.

Evans RS, et al., "Preventing Adverse Drug Events in Hospitalized Patients," *Annals of Pharmacotherapy* 28 (Apr. 1994): 523–527.

Evans RS, et al., "Prevention of Adverse Drug Events Through Computerized Surveillance," *Proc Annu Symp Copmut Appl Med Care* 16 (1992): 437–41.

Evans RS et al., "Development of an Automated Antibiotic Consultant," *M.D. Computing* 10.1 (1993): 17–22.

Evans RS, et al., "Using a Hospital Information System to Assess the Effects of Adverse Drug Events," *Proc Annu Symp Comput Appl Med Care* 17 (1993): 161–65.

Evans RS, et al., "Reducing the Duration of Prophylactic Antibiotics through Computer Monitoring of Surgical Patients," *DICP, The Annuals of Pharmacotherapy* 24 (Apr. 1990): 351–354.

Harbarth S, et al., "Clinical and Economic Outcomes of Conventional Amphotericin B–Associated Nephrotoxicity," *CID* 35 (Dec. 15, 2002): e120–127.

Hongsermeier TM, et al., "TheraDoc Expert Systems: The Cornerstone of a Successful Infection Management and Patient Safety Strategy," *White Paper*, Salt Lake City: TheraDoc, Inc. (2003): 1–10.

Kelly DL, et al., "Reengineering a Surgical Service Line: Focusing on Core Process Improvement," *American Journal of Medical Quality* 12.2 (1997): 120–29.

Larsen RA, et al., "Improved Perioperative Antibiotic Use and Reduced Surgical Wound Infections Through Use of Computer Decision Analysis," *Infect Control Hosp Epidemiol* 10.7 (1989): 316–320.

Leader WG, et al., "Integrating Pharmacokinetics into Point–of–Care Information Systems," *Clin. Pharmacokinet.* 31.3 (Sep. 1996): 165–173.

Pestotnik SL, et al., "Expert Clinical Decision Support Systems to Enhance Antimicrobial Stewardship Programs," *Pharmacotherapy* 25.8 (2005): 1116–25.

Pestotnik SL, et al., "Expert Clinical Decision Support Systems to Enhance Antimicrobial Stewardship Programs," *Society of Infectious Diseases Pharmacists Newsletter* 14.3 (Winter 2005): 2–7.

Pestotnik SL, et al., "Prospective Surveillance of Imipenem/Cilastatin Use and Associated Seizures Using a Hospital Information System," *Annals of Pharmacotherapy* 27 (Apr. 1993): 497–501.

Pestotnik, et al., "Therapeutic Antibiotic Monitoring: Surveillance Using a Computerized Expert System," *American Journal of Medicine* 88 (Jan. 1990): 43–48.

Evans RS, et al., "Computer Surveillance of Hospital–Acquired Infections and Antibiotics Use," *JAMA* 256.8 (Aug. 22/29, 1986): 1007–1011.

Evans RS, et al., "Evaluating the Impact of Computer–based Drug Monitoring on the Quality and Cost of Drug Therapy," *Hospital Information Systems* (1995): 201–220.

Classen DC, et al., "The Computer–Based Patient Record: An Essential Technology for Hospital Epidemiology," *Hospital Epidemiology and Infection Control* Ed. CG Mayhall, Williams & Williams, Baltimore, MD (1996): 123–137.

Harbarth S, et al., "The Epidemiology of Nephrotoxicity Associated with Coventional Amphotericin B Therapy," *American Journal of Medicine* 111 (Nov. 2001): 528–534.

Pestotnik S, "The Future of ID Pharmacy Practice: Putting Decisions in Decision Support," [editorial ] *Society of Infectious Diseases Pharmacists Newsletter* 5.3 (Fall 1995): 2–3.

Bates DW, et al., "The Costs of Adverse Drug Events in Hospitalized Patients. Adverse Drug Events Prevention Study Group," *JAMA* 277.4 (Jan. 22, 1997): 1 <http://jama.ama-assn.org/cgi/content/abstract/277/4/307>.

Burke JP, "Hospitals Enter the War Against Antibiotic Resistance," [editorial review] *Current Opinion on Infectious Diseases* 8 (1995): 269–271.

Classen, DC, et al., "The Computer–Based Patient Record: An Essential Technology for Hospital Epidemiology," *Hospital Epidemiology and Infection Control 2E*. Ed. C. Glen Mayhall. Lippiacott Williams & Williams, Philadelphia, PA (1999): 141–154.

Naranjo CA, et al., "A Method for Estimating the Probability of Adverse Drug Reaction," *Clinical Pharmacology and Therapeutics* 30.2 (Aug. 1981): 239–245.

Evans RS, et al., "Experience with a Computer–Assisted Antiinfective Agent Management Program," *Computer–Assisted Decision–Making Activated by Clinical Laboratory Findings. Clin Chem Lab Med* Symposium Abstracts –IFCC–WorldLab '99. Firenze. 37 –Special Supplement (Jun. 6–11, 1999): S6.

Classen DC, et al., "Adverse Effects of Intravenous Erythromycin in Hospital Patients: Attributable Costs and Excess Length of Stay," Abstracts of the 36$^{th}$ ICAAC, American Society for Microbiology, New Orleans, Louisiana, Session 112 (Sep. 15–18, 1996): Article N19: 296.

Pestotnik SL, et al., "Adverse Effects of Intravenous Vancomycin (IVV) in Hospital Patients: Attributable Costs and Excess Length of Stay," *Clinical Infectious Diseases*, Abstracts of the IDSA 35$^{th}$ Annual Meeting 25.2 (Aug. 1997) Article 376: 424.

Classen DC, et al., "The Impact of Managed Care and Capitation on the Practice of Infectious Disease: Strategies for Managing Clinical Care," Abstracts –35$^{th}$ Interscience Conference on Antimicrobial Agents and Chemotherapy an Annual Meeting of the American Society for Microbiology San Francisco, CA (Sep. 17–20, 1995): Article S19–352.

Pestotnik SL, et al., "A Five–Year Analysis of Parental Anti–Infective Use at a Tertiary Care Hospital," Abstracts of the 33$^{rd}$ ICAAC. New Orleans, LA (Oct. 17–20, 1993), 634–235.

Pestotnik SL, et al., "Surveillance of Imipenem–associated Seizures in a Large Cohort of Hospitalized Patients," Abstracts of the 1992 ICAAC, The 32$^{nd}$ Interscience Conference on Antimicrobial Agents and Chemotherapy. Anaheim, CA (Oct. 11–14, 1992), 530–199.

Classen DC, et al., "Clinical Evaluation of a Computerized Antibiotic Selection Program in a Large Teaching Hospital," Abstracts of the 1992 ICAAC, The 32$^{nd}$ Interscience Conference on Antimicrobial Agents and Chemotherapy. Anaheim, CA (Oct. 11–14, 1992), Article 532: 199.

Burke JP, et al., "Evaluation of Therapeutic Antibiotic Substitution by Microcosting Using an Automated Hospital Database," Abstracts of the 1991 ICAAC, The 31$^{st}$ Interscience Conference on Antimicrobial Agents and Chemotherapy. Chicago, IL (Sep. 29 –Oct. 2, 1991), Article 407: 167.

Burke JP, et al., "Inappropriate Antibiotic Therapy: Detection Using Computer Algorithms," *Clinical Research* 36.1 (Jan. 1988): 28A.

Evans RS, et al., "The Evaluation of an Automated Antibiotic Consultant," National Technical Information Services, Departments of Medical Informatics, Infectious Diseases, and Pharmacy, LDS Hospital and University of Utah School of Medicine, Salt Lake City, UT (1994): 1–25.

Classen DC, et al., "Case 12.1: LDS Hospital: Institution–Wide Antibiotic Management," *Transforming Health Care Through Information Case Studies* NM Lorenzi, et al. Ed. Springer–Verlag, New York, NY (1995): 322–332.

Evans RS, et al., "Evaluating the Impact of Computer–based Drug Monitoring on the Quality and Cost of Drug Therapy," *Hospital Information Systems: Design and Development Characteristics: Impact and Future Architecture*. Medical Artifical Intelligence Series. Amsterdam: Elsevier. 2 (1998): 1–20.

Burke JP, et al., Reply to Letters. *JAMA* 277.17 (May 7, 1997): 1351–1353.

Burke JP, "Evaluation of the Impact of Implementation of a Comprehensive Computerized Antibiotic Management Program at Intermountain Health Care," Healthcare Information and Management Systems Society Proceedings 1 (1997): 18–24.

Gundlapalli AV, et al., "A Rule–based Computer System to Facilitate Public Health Surveillance: Deployment by a Hospital Infection Control Unit," upon information and belief, available at least as early as 2001.

Tettelbach W, et al., "Usage Evaluation of a Computerized Clinical Decision Support System (CDSS) Utilized by the Rural Antibiotic Decision–Support & Resistance (RADAR) Project," upon information and belief, available at least as early as 2001.

"ADE Assistant," www.theradoc.com. Nov. 13, 2005. <http://www.theradoc.com/products/products_ade.html>.

"Antibiotic Assistant –Integrated Model," www.theradoc.com. Nov. 13, 2005. <http://www.theradoc.com/products/products_integrated.html>.

"Antibiotic Assistant –Antibiotic Assistant Overview." www.theradoc.com. Nov. 13, 2005. <http://www.theradoc.com/products/products abxassist.html>.

Burke JP, et al., "Evaluation of the Financial Impact of Ketorolac Tromethamine Therapy in Hospitalized Patients," Rpt. from *Clinical Therapeutics* 18.1 (1996): 197–211.

Burke JP, et al., "The Pharmacy and Drug Usage," Assessing Quality Health Care: Perspectives for *Clinicians*. Baltimore: Williams & Wilkins (1991): 509–20.

Classen DC, et al., "Antibiotic Prophylaxis and Surgical Wound Infections," [To the Editor:] *New England Journal of Medicine* 327.3 (Jul. 16, 1992): 205–206.

Classen DC, et al., "Prophylactic Antibiotics Used to Prevent Surgical Wound Infections," *Clinical Practice Improvement: A New Technology for Developing Cost–Effective Quality Health Care* New York: Faulkner & Gray (1994): 217–21.

Gundlapalli AV, et al., "Hospital Electronic Medical Record––Based Public Health Surveillance System Deployed During the 2002 Winter Olympic Games," Presented in part at the 2003 APIC Conference, San Antonio, TX, Session 2301 (Jun. 10, 2003): 1–17.

Lo TS., et al., "Secular Trends of Enterococcal Urinary Tract Infection: A Ten–Year Study [Abstract], " American Society for Microbiology, 1$^{st}$ International ASM Conference on Enterococci, available at least as early as Dec. 6, 1999: 1.

Pestotnick SL, et al., "Medical Informatics: Meeting the Information Challenges of a Changing Health Care System," *Journal of Informed Pharmacotherapy* 2 (2000): 1.

Pestotnik SL, (Aug. 1993). "Computer–Based Alerts for Drug Dosing in Renal Impairment," unpublished masters thesis, University of Utah, Salt Lake City, Utah, United States: 1–62.

Pestotnik SL, "Role of Information Systems in Reducing Adverse Drug Events," *Improving the Quality of the Medication Use Process: Error Prevention & Reducing Adverse Drug Events*. New York: Pharmaceutical Products Press/Haworth Press, Inc. (1998): 183–91.

Pestotnik SL, et al., "Medical Informatics, Decision Support, and Quality of Care: Clinicians's Perspective," *International Pharmaceutical Abstracts,* Information Processing and Literature, 3505425: 817.

Riley DK, et al., "The Effect of Improved Prophylactic and Therapeutics Antibiotic Use on Hospital Microbial Resistance Patterns," *Infection Control and Hospital Epidemiology,* S2 (Apr. 1994): P26.

"HELP's Pharmacy System," *I/O, An Update from IHCNET,* vol. 1, No. 4, Jul/Aug. 1989, pp. 1–2, 4.

Bleigh, Howard L., M.D., "The Computer as a Consultant," *Seminars in Medicine of the Beth Israel Hospital, Boston,* vol. 284, No. 3, Jan. 21, 1971, pp. 141–147.

Bleigh, Howard L., M.D., et al., "Clinical Computing in a Teaching Hospital," *The England Journal of Medicine,* vol. 312, No. 12, Mar. 21, 1985, pp. 756–764.

Bradshaw, Karen E., et al., "Development of a Computerized Laboratory Alerting System," *Computers and Biomedical Research,* vol. 22, 1989, pp. 575–587.

Gardner, Reed M., "Computerized Data Management and Decision Making in Critical Care," *Surgical Clinics of North America,* vol. 65, No. 4, Aug. 1985, pp. 1041–1051.

McDonald, Clement J., M.D., et al., "The Regenstrief Medical Records," M.D. *Computing,* vol. 5, No. 5, 1988, pp. 34–47.

Stead, William W., M.D., et al., "Computer–Based Medical Records: The Centerpiece of TMR," *M.D. Computing,* vol. 5, No. 5, 1988, pp. 48–61.

Yu, Victor L., M.D., et al., "Antimicrobial Selection by a Computer –A Blinded Evalution by Infectious Experts," *JAMA,* vol. 242, No. 12, Sep. 21, 1979, pp. 1279–1282.

* cited by examiner

TABLE 1

| # | Statement | Rule |
|---|-----------|------|
| 1 | Coverage includes Legionella and potentially resistant gram negative rods | If ventilator or non-ventilator HAP and organism unknown and interval from admission>5 days and (severity is severe or recent prior antibiotics) and Legionella cases identified, then (ceftazidime + ciprofloxacin), (aztreonam + ciprofloxacin (admitted through intravenous)(IV)), piperacillin/tazobactam + macrolide IV |
| 2 | Coverage includes resistant gram negative rods because of risk factors. | If ventilator or non-ventilator HAP and organism unknown and interval from admission>5 days and (severity is severe or recent prior antibiotics), then piperacillin/tazobactam, (ceftazidime + ciprofloxacin), (aztreonam + ciprofloxacin IV) |
| 3 | Coverage includes hospital-acquired gram negative rods. | If ventilator or non-ventilator HAP and organism unknown and interval from admission>5 days, then piperacillin/tazobactam, ceftazidime, ciprofloxacin IV. |
| 4 | The recommended therapy is highly active against anaerobes. The onset of aspiration pneumonia is relatively soon after admission. | If ventilator or non-ventilator HAP and organism unknown and admission interval < 6 days and aspiration, then (clindamycin + FQ IV), (metronidazole + FQ IV), ampicillin/sulbactam, (metronidazole IV + $3^{rd}$ gen ceph IV) (clindamycin + aztreonam) |
| 5 | Therapy directed toward community- and hospital-acquired organisms because of relatively short interval since admission. | If ventilator or non-ventilator HAP and organism unknown and interval from admission <6 days, then FQ IV, $3^{rd}$ gen ceph IV + macrolide (admitted orally)(PO)), (clindamycin IV + aztreonam) |
| 6 | Therapy directed against hospital-acquired resistant gram negative rods | If ventilator and organism unknown and sputum gram stain GNR, then imipenem, (ceftazidime + ciprofloxacin), (ceftazidime + gentamicin), (ciprofloxacin + gentamicin) |
| 7 | Empiric antibiotic coverage weighted toward gram positive cocci because of sputum gram stain results | If ventilator and organism unknown and sputum gram stain GPC, then (vancomycin + ceftazidime), (vancomycin + ciprofloxacin), (nafcillin + ciprofloxacin), (nafcillin + ceftazidime) |

FIG. 6A

TABLE 1 (cont'd)

| # | Statememt | Rule |
|---|---|---|
| 8 | Broad spectrum antibiotics recommended because of patient location and/or risk factors. | If CAP and (ICU or (ward and neutropenia)) and organism unknown, then ($3^{rd}$ gen ceph + FQ IV), (piperacillin/tazobactam + macrolide IV), (imipenem + macrolide IV), (vancomycin + ciprofloxacin IV) |
| 9 | The recommended therapy is highly active against anaerobes. The infection is community-acquired. | If CAP and inpatient and organism unknown and (aspiration or putrid sputum or lung abscess suspected), then clindamycin IV, (penicillin + metronidazole), ampicillin/sulbactam |
| 10 | The recommended therapy is highly active against anaerobes | If CAP and outpatient and organism unknown and aspiration, then amoxicillin/clavulanate, clindamycin PO, (amoxicillin + metronidazole) |
| 11 | Empiric antibiotics for hospitalized patients with community-acquired pneumonia includes coverage for common pyogenic organisms such as *S. pneumoniae* as well as "atypical" pathogens. | If CAP and ward and organism unknown, then ($3^{rd}$ gen ceph IV + macrolide PO), (FQ IV), (vancomycin + macrolide IV), |
| 12 | The recommended oral antibiotic is active against most pathogens associated with community-acquired pneumonia. | If CAP and outpatient and organism unknown and age<60, then macrolide PO, amoxicillin, FQ PO not cipro, doxycycline. |
| 13 | The recommended oral antibiotic is active against pathogens commonly associated with community-acquired pneumonia among patients within this age range. | If CAP and outpatient and organism unknown, and age>=60, then amoxicillin-clavulanate, FQ PO not cipro, cefuroxime PO, macrolide PO |
| 14 | Patients who do not respond to outpatient macrolide or beta-lactam therapy may be treated with a fluoroquinolone or, alternatively, admitted to the hospital for intravenous therapy and further | If CAP and outpatient and organism unknown and macrolide/pencillin treatment failure, then FQ PO not cipro, ($3^{rd}$ gen ceph IV + macrolide PO) |

FIG. 6B

TABLE 1 (cont'd)

| # | Statement | Rule |
|---|---|---|
| 15 | The recommended oral antibiotic is active against most pathogens associated with community-acquired pneumonia. | If CAP and outpatient and organism unknown and one or more co-morbidities, then FQ PO not cipro, macrolide, amoxicillin/clavulanate. |
| 16 | The recommended therapy is effective against Legionella. If the patient is critically ill, add rifampin 600 mg PO/day | If CAP or HAP and organism Legionella, then FQ IV, macrolide IV, macrolide IV + FQ IV, macrolide IV + ciprofloxacin, |
| 17 | The recommended therapy is active against P. aeruginosa and S. aureus | If organism P. aeruginosa and S. aureus, then piperacillin/tazobactam, imipenem, (ceftazidime + vancomycin), (ciprofloxacin IV + vancomycin) |
| 18 | The recommended therapy is active against P. aeruginosa and S. pneumoniae | If organism P. aeruginosa and S. pneumoniae, then imipenem, piperacillin, ceftazidime + FQ IV not cipro, |
| 19 | The recommended therapy is highly active against P. aeruginosa. Combination antibiotic therapy is generally preferred for treatment of pseudomonal pneumonia to reduce the likelihood of emergence of resistance. | If (CAP or HAP) and organism P. aeruginosa, then (ceftazidime + tobramycin), (piperacillin + tobramycin), (imipenem + tobramycin), (ciprofloxacin IV + tobramycin), (ceftazidime + ciprofloxacin IV), (piperacillin + ciprofloxaxin IV), (imipenem + ciprofloxacin) |
| 20 | The recommended therapy is active against Acinetobacter. | If CAP or HAP and organism Acinetobacter, then imipenem, ceftazidime, ampicillin/sulbactam |
| 21 | The recommended therapy is active against gram negative rods which may become resistant to 3$^{rd}$ generation cephalosporins through over-production of beta-lactamases. | If CAP or HAP and organism Enterobacter or Serratia or Citrobacter, then cefipime, imipenem, 3$^{rd}$ gen ceph + FQ IV, 3$^{rd}$ gen ceph + gentamicin |
| 22 | The recommended therapy is active against gram negative rods. | If CAP or HAP and organism E. coli or Klebsiella, then 3$^{rd}$ gen ceph IV, FQ IV, piperacillin/tazobactam, imipenem |

FIG. 6C

TABLE 1 (cont'd)

| # | Statement | Rule |
|---|---|---|
| 23 | The recommended therapy is active against Stenotrophomonas | If CAP or HAP and organism Stenotrophomonas, then TMP/SMX IV, doxycycline, ticarcillin/clavulanate |
| 24 | The recommended therapy is active against gram negative rods. | If CAP or HAP and organism other GNR, then cefipime, imipenem, FQ IV, $3^{rd}$ gen ceph + gentamicin |
| 25 | The recommended therapy is active against S. aureus. Vancomycin is preferred when the rate of methicillin resistance exceeds 10%. | If (CAP or HAP) and organism S. aureus and susceptibility unknown, vancomycin, nafcillin, cefazolin |
| 26 | The recommended therapy is active against S. aureus. | If (CAP or HAP) and organism S. aureus and susceptibility known, then oxacillin, vancomycin, linezolid, dalfopristin/quinupristin |
| 27 | The recommended therapy is active against H. influenzae | If ((CAP and inpatient) or HAP) and organism H. influenzae, then $3^{rd}$ gen ceph, FQ IV, ampicillin. |
| 28 | The recommended therapy is active against H. influenzae | If ((CAP and inpatient) or HAP) and organism H. influenzae, then $3^{rd}$ gen ceph, FQ IV, ampicillin. |
| 29 | The recommended therapy is appropriate for S. pneumoniae when susceptibility is not yet known. | If ((CAP and inpatient) and (((CAP and inpatient) or HAP) and organism S. pneumoniae and susceptibility unknown), then $3^{rd}$ gen ceph IV, FQ IV not cipro, macrolide IV, vancomycin |
| 29 | The recommended anti-pneumococcal antibiotic is based on the indicated susceptibility results. | If ((CAP and inpatient) or HAP) and organism S. pneumoniae and susceptibility known, then ampicillin, $3^{rd}$ gen ceph IV, macrolide IV, FQ IV not cipro, vancomycin |
| 30 | The recommended oral therapy is appropriate for S. pneumoniae when susceptibility is not yet known. | If CAP and outpatient and organism S. pneumoniae and susceptibility unknown and outpatient, then FQ PO not cipro, amoxicillin, macrolide PO, cefuroxime PO. |
| 31 | The recommended oral therapy is active against S. | If CAP and outpatient and organism S. pneumoniae and susceptibility known and outpatient, then |

FIG. 6D

TABLE 1 (cont'd)

| # | Statement | Rule |
|---|---|---|
| 31 | The recommended oral therapy is active against *S. pneumoniae* | If CAP and outpatient and organism *S. pneumoniae* and susceptibility known and outpatient, then amoxicillin, macrolide PO, FQ PO not cipro |
| 32 | The recommended therapy is reliably active against group A strep. | If organism Group A Strep, then Penicillin G, ampicillin IV, clindamycin IV, cefazolin. |
| 33 | The recommended therapy is active against Neisseria meningitidis | If organism Neisseria meningitidis, then penicillin G, $3^{rd}$ gen ceph, FQ IV |
| 34 | The recommended therapy is active against Moraxella | If organism and ((CAP and inpatient) or HAP) and organism Moraxella catarrhalis, then $3^{rd}$ gen ceph, ampicillin/sulbactam, FQ IV |
| 35 | The recommended therapy is active against Moraxella | If organism and CAP and outpatient and organism Moraxella catarrhalis, then cefuroxime PO, TMP/SMX, amoxicillin/clavunalate, FQ PO |
| 36 | The recommended therapy is active against mycoplasma | If CAP or HAP and organism mycoplasma, then macrolide PO, doxycycline PO, FQ PO |
| 37 | The recommended therapy is active against Chlamydia | If CAP or HAP and organism Chlamydia psittaci or Chlamydia pneumoniae, then doxcycline PO, macrolide PO, FQ PO |
| 38 | The recommended therapy is active against Q fever | If CAP and organism Coxiella burnetii, then doxcycline PO, chloramphenicol |
| 39 | The recommended therapy is active against influenza virus. | If CAP or HAP and organism influenza, then rimantidine, oseltamivir |

FIG. 6E

TABLE 2 (Mitigating factor rules (optionally sequential))

If HAP and non-ventilator, then query "Clinically severe?", Interval from admission > 5 days?, Recent prior antibiotics?, Have nosocomial Legionella cases been identified at this institution and is the patient immunosuppressed?

If HAP and ventilator, then query "Clinically severe?", Interval from admission > 5 days?, Recent prior antibiotics?, "Sputum gram stain demonstrates gram negative rods?", "Sputum gram stain demonstrates gram positive cocci?"

If CAP, then query "Is the patient neutropenic?", "Did the patient fail treatment with penicillin or macrolide type antibiotics?, "Putrid sputum or lung abscess suspected?"

FIG. 7

TABLE 3 (Interpretation of susceptibility rules (not sequential))

1   If ampicillin MIC > 1 ug/ml, then interpret S. pneumoniae as resistant to ampicillin
2   If ceftriaxone or cefotaxime MIC > 1.0 ug/ml, then interpret S. pneumoniae as resistant to $3^{rd}$ gen ceph

FIG. 8

TABLE 4 (Duration rules (sequential))

1   If organism legionella or gram negative rod or Mycoplasma or Chlamydia pneumoniae or Chlamydia psittaci or Coxiella burnetti then state "Recommended duration is 21 days"

2   If lung abscess suspected, state "Duration is based on response to therapy"

3   State "Recommended duration of therapy is 14 days"

FIG. 9

TABLE 5 (Caveats (not sequential))

1    If inpatient, then caveat "If clinical response is satisfactory after 2 – 3 days and GI absorption is adequate, therapy may be switched to an oral agent based on organism identification and susceptibility 2    If aspiration and inpatient and interval from admission >5 days and recommended antibiotic not imipenem or piperacillin/tazobactam, then caveat "Aspiration pneumonia in hospitalized patients is most often due to aerobic gram negative and gram positive pathogens which colonize the oropharynx after admission. If anaerobes strongly suspected then clindamycin or metronidazole may be added"

3    If organism *S. pneumoniae* and susceptibility unknown, then caveat "Cefotaxime or ceftriaxone are adequate for empiric therapy of pneumococcal pneumonia because the prevalence of high level cefotaxime or ceftriaxone resistance (MIC > 2 ug/ml) is still less than 5% in adults.

FIG. 10

Etiologic classification
    Organism identified                                    Organism uncertain/emperic therapy Bacteria Gram negative rods
                    E. coli
                    Klebsiella oytoca
                    Klebsiella pneumoniae
                    Enterobacter spp.
                    Proteus mirablis
                    Pseudomonas aeruginosa
                    Other
                        Acinetobacter spp.
                        Burkholderia cepacia
                        Citrobacter spp.
                        Gardenella vaginalis
                        Haemophilus influenzae
                        Hemophilus parainfluenzae
                        Morganella spp.
                        Proteus vulgaris
                        Providencia spp.
                        Salmonella spp.

Gram negative cocci
                        Neisseria gonorrhoeae

Gram positive cocci
                        Enterococcus faecalis
                        Staphylococcus aureus
                        Staphyloccucs coagulase-negative
                        Staphylococcus saprophyticus
                        Staphylococcus epidermidis
                        Other
Streptococci group B Gram positive rods
                        Clostridium perfringens
                        Corynebacterium urealyticum
                        Lactobacillus spp.

Acid-fast bacteria
                        Mycobacterium tuberculosis

FIG. 12A

```
Fungi
        Candida spp.
        Candida albicans
        Candida parapsilosis
        Candida pseudotropicalis
        Candida tropicalis
        Candida glabrata
        Candida krusei
        Candida norvegensis
        Candida guilliermondi
        Candida lusitaniae Non-candida spp.
        Actinomyces spp.
        Aspergillus spp.
        Blastomyces dermatitidis
        Cryptococcus neoformans Parasites
        Chlamydia trachomatis
        Schistosoma haematobium Viral
        Adenovirus
```

FIG. 12B

TABLE 6 (Anti-bacterial Antibiotic Selection Rules and Statements)

| # | Statement | Rule |
|---|---|---|
| 1 | No objective evidence of active urinary tract infection. None of the indications to treat asymptomatic infection are present. | Infection asymptomatic and culture is negative, then state "Antibiotic therapy not recommended on the basis of the available information" |
| 2 | No objective evidence of active urinary tract infection. None of the indications to treat asymptomatic infection are present. | Infection asymptomatic "and organism uncertain" and none of the factors listed in table "asymptomatic" present then state "Antibiotic therapy not recommended on the basis of the available information." |
| 3 | More than 3 positive organisms in a urine culture typically indicates contamination. | If >3 organisms identified, then state "Recommend repeat culture" |
| 4 | Antibiotic therapy highly active against both gram negative rods and gram positive cocci; recommended because of risk factors and upper tract infection. | (Organism uncertain or urine collection none) and upper tract infection and (obstruction or abnormal anatomy or recent urologic surgery), then recommend (vancomycin and ciprofloxacin IV), piperacillin/tazobactam, (vancomycin and gentamicin) |
| 5 | Antibiotic therapy highly active against both gram negative rods and gram positive cocci; recommended because of risk factors and upper tract infection. | (Organism uncertain or urine collection none) and upper tract infection and renal transplant, recommend piperacillin/tazobactam, (vancomycin and ciprofloxacin IV), (vancomycin and gentamicin) |
| 6 | Sexually active young adults between the ages of >17 and age <30 with symptomatic sterile pyuria are at increased risk for *Chlamydia trachomatis* urethritis. Recommended antibiotic is active against suspected organisms associated with this clinical syndrome. | Organism uncertain and culture is negative and urine collection is clean catch and therapy is outpatient and infection is lower tract and age >17 and age <30, then recommend doxycycline PO, azithromycin PO, FQ PO |

FIG. 13A

TABLE 6 (Anti-bacterial Antibiotic Selection Rules and Statements)

| # | Statement | Rule |
|---|---|---|
| 7 | The recommended antibiotic is active against organisms commonly associated with lower tract urinary infections. FQ is recommended first line therapy in the absence of contraindications when the prevalence of E.coli resistance to TMP/SMX is at least 20% | (Organism uncertain or urine collection none) and lower tract/asymptomatic, then recommend FQ PO, sulfamethoxazole-trimethoprim PO, nitrofurantoin PO, amoxicillin/clavulanate PO, cephalexin PO |
| 8 | The recommended oral antibiotic therapy is active against organisms commonly associated with urinary tract infection and is superior to oral beta-lactam antibiotics for treatment of upper tract infection. | (Organism uncertain or urine collection none) and upper tract and outpatient, then recommend FQ PO, sulfamethoxazole-trimethoprim PO, amoxicillin-clavulanate PO, cephalexin PO |
| 9 | The recommended intravenous antibiotic therapy is highly active against organisms commonly associated with upper tract urinary infection. | (Organism uncertain or urine collection none) and upper tract and inpatient, then recommend FQ IV, $3^{rd}$ gen ceph, sulfamethoxazole-trimethoprim IV, gentamicin IV + vancomycin IV) |
| 10 | The recommended antibiotic therapy is active against Pseudomonas aeruginosa and gram positive organisms. | Organism pseudomonas aeruginosa and (GPC or GPR) and upper tract, then recommend piperacillin-tazobactam IV, imipenem IV, (vancomycin IV + ciprofloxacin IV), consult |
| 11 | The recommended antibiotic therapy is active against susceptible Pseudomonas aeruginosa and gram positive organisms. If unable to take oral ciprofloxacin, then intravenous therapy recommended. | Organism pseudomonas aeruginosa and (GPC or GPR) and lower tract, then recommend ciprofloxacin PO, ciprofloxacin PO + amoxicillin/clavulanate PO |

FIG. 13B

TABLE 6 (Anti-bacterial Antibiotic Selection Rules and Statements)

| # | Statement | Rule |
|---|---|---|
| 18 | The recommended antibiotic therapy is active against gram negative rods. FQ is recommended first line therapy in the absence of contraindications when the prevalence of E.coli resistance to TMP/SMX is at least 20%. | Organism GNR and susceptibility not known and lower tract/asymptomatic then recommend FQ PO, sulfamethoxazole-trimethoprim PO, nitrofurantoin PO, amoxicillin/clavulanate PO, cephalexin PO |
| 19 | TMP/SMX is recommended first line therapy when the gram negative rod is known to be susceptible. Alternative antibiotic agents are recommended when the organism is resistant to TMP/SMX or a contraindication to TMP/SMX is present. | Organism GNR and susceptibility results known and lower tract/asymptomatic, then recommend sulfamethoxazole-trimethoprim PO, FQ PO, cephalexin PO, nitrofurantoin PO |
| 20 | The recommended antibiotic therapy is active against susceptible enterococci and staphylococci. | Organism enterococcus and upper tract and (Staphylococcus aureus or Staph coagulase-negative) and susceptibility not known, then recommend vanomycin IV, ampicillin-sulbactam IV, consult |
| 21 | The recommended antibiotic therapy is active against enterococci and staphylococci. Ampicillin/sulbactam is preferred to vancomycin for treatment of beta-lactam susceptible staphylococci. | Organism enterococcus and upper tract and (Staphylococcus aureus or Staph coagulase-negative) and susceptibility known, then recommend ampicillin-sulbactam IV, vancomycin IV, quinupristin IV *, consult * |
| 22 | The recommended antibiotic therapy is active against susceptible enterococci and staphylococci. | Organism enterococcus and lower tract and (Staphylococcus aureus or Staph coagulase-negative), then recommend amoxicillin-clavulanate PO, FQ PO, doxycycline PO, vancomycin PO |

FIG. 13C

TABLE 6 (Anti-bacterial Antibiotic Selection Rules and Statements)

| # | Statement | Rule |
|---|---|---|
| 23 | The recommended antibiotic therapy is active against Staphylococcus aureus. Vancomycin is first line therapy for inpatient upper tract infection pending susceptibility. | Organism Staphylococcus aureus and inpatient and upper tract infection and susceptibility not known, then recommend vancomycin IV, Nafcillin IV, Cefazolin IV, consult. |
| 24 | The recommended antibiotic therapy is active against Staphylococcus aureus. Nafcillin is preferred to vancomycin for susceptible organisms. | Organism Staphylococcus aureus and inpatient and upper tract infection and susceptibility known, then recommend nafcillin IV, cefazolin IV, vancomycin IV, quinupristin IV *, Consult *. |
| 25 | The recommended antibiotic therapy is active against susceptible Staphylococcus aureus. | Organism Staphylococcus aureus and outpatient and lower tract/asymptomatic infection then recommend, dicloxacillin PO, cephalexin PO FQ PO, sulfamethoxazole-trimethoprim PO. |
| 26 | The recommended intravenous antibiotic therapy is active against susceptible Staphylococcus aureus. | Organism Staphylococcus aureus and outpatient and upper tract, then recommend nafcillin IV, cefazolin IV, vancomycin IV, quinupristin IV *, consult *. |
| 27 | The recommended therapy is active against Staphylococcus saprophyticus. | (Organism Staphylococcus saprophyticus or (organism Staph coagulase-negative and female and age >15 and <50 years and no urinary obstruction and no abnormal anatomy and urine is clean catch)) and ((inpatient and lower tract/asymptomatic) or (outpatient)), then recommend sulfamethoxazole-trimethoprim PO, cephalexin PO, FQ PO. |
| 28 | The recommended intravenous therapy is active against Staphylococcus saprophyticus. | (Organism Staphylococcus saprophyticus or (organism Staph Coagulase-negative and female and age >15 and <50 years and no urinary obstruction and no abnormal anatomy and urine is clean catch)) and inpatient and upper tract, then recommend cefazolin IV, |

FIG. 13D

TABLE 6 (Anti-bacterial Antibiotic Selection Rules and Statements)

| # | Statement | Rule |
|---|---|---|
| 29 | The recommended therapy is active against Staphylococcus coagulase negative. This organism is usually resistant to beta-lactam antibiotics. | Organism Staph coagulase-negative and susceptibility not known, then recommend vancomycin IV, consult. |
| 30 | The recommended intravenous antibiotic therapy is active against susceptible coagulase negative staphylococci. Cefazolin is preferred to vancomycin for susceptible organisms. | Organism Staph coagulase-negative and susceptibility known and upper tract, then recommend cefazolin IV, vancomycin IV, consult. |
| 31 | The recommended antibiotic therapy is active against susceptible coagulase negative staphylococci. | Organism Staph coagulase-negative and susceptibility known and lower tract/asymptomatic, then recommend dicloxacillin PO, sulfamethoxazole-trimethoprim PO, doxycycline PO, vancomycin PO, consult. |
| 32 | The recommended intravenous antibiotic therapy is active against susceptible enterococci. | Organism enterococcus and upper tract infection, then recommend ampicillin IV, vancomycin IV, consult. |
| 33 | The recommended antibiotic therapy is active against susceptible enterococci. | Organism enterococcus and lower tract/asymptomatic infection, then recommend amoxicillin PO, nitrofurantoin PO, doxycycline PO. |
| 34 | The recommended antibiotic therapy is active against group B streptococci. | Organism Streptococci Group B and upper tract, then recommend ampicillin IV, cefazolin IV, vancomycin IV. |

FIG. 13E

TABLE 6 (Anti-bacterial Antibiotic Selection Rules and Statements)

| # | Statement | Rule |
|---|---|---|
| 35 | The recommended antibiotic therapy is active against group B streptococci. | Organism Streptococci Group B and lower tract/asymptomatic, then recommend amoxicillin PO, cephalexin PO, sulfamethoxazole-trimethoprim PO. |
| 36 | The recommended antibiotic therapy is active against Corynebacterium urealyticum. | Organism Corynebacterium and susceptibility not known, then recommend vancomycin IV. |
| 37 | The recommended antibiotic therapy is active against Corynebacterium urealyticum. Ampicillin is preferred to vancomycin for susceptible organisms. | Organism Corynebacterium and susceptibility known, then recommend ampicillin IV, vancomycin IV, consult. |
| 38 | The recommended antibiotic therapy is active against lactobacillus. | Organism lactobacillus and lower tract, then recommend amoxicillin-PO, clarithromycin PO, clindamycin PO. |
| 39 | The recommended antibiotic therapy is active against lactobacillus. | Organism lactobacillus and upper tract, then recommend ampicillin IV, clindamycin IV, erythromycin IV. |
| 40 | The recommended antibiotic therapy is active against Staphylococcus saprophyticus which is the likely organism. | Organism GPC not further identified and female and age >15 and <50 years and clean catch and outpatient, then recommend sulfamethoxazole-trimethoprim PO, amoxicillin-clavulanate PO. |
| 41 | The recommended intravenous antibiotic therapy is active against gram positive organisms. | Organism one or more GPC or GPR not further identified and upper tract infection, then recommend ampicillin-sulbactam IV, vancomycin IV. |
| 42 | The recommended antibiotic therapy is active against gram positive organisms. | Organism one or more GPC or GPR not further identified and lower tract/asymptomatic infection, then recommend amoxicillin-clavulanate PO, nitrofurantoin PO, doxycycline PO |

FIG. 13F

TABLE 7 (Candida and Miscellaneous Organism Rules (Optionally Sequential))

| | | |
|---|---|---|
| 1 | Antibiotic therapy highly active against both gram negative rods and gram positive cocci; recommended because of risk factors and upper tract infection. | Organism chlamydia, then recommend doxycycline PO, azithromycin PO, amoxicillin PO. |
| 2 | The recommended antibiotic therapy is active against Staphylococcus aureus. Vancomycin is first line therapy for inpatient upper tract infection pending susceptibility. | Organism mycobacterium, then recommend consult |
| 3 | The recommended antibiotic therapy is active against susceptible Pseudomonas aeruginosa and gram positive organisms. If unable to take oral ciprofloxacin, then intravenous therapy recommended. | Organism Candida and lower tract and not Foley catheter, then recommend fluconazole PO, amphotericin B IV, consult *. |
| 4 | The recommended antibiotic therapy is active against susceptible Pseudomonas aeruginosa and gram positive organisms. | Organism Candida and lower tract and Foley catheter, then recommend fluconazole PO, amphotericin B IV, bladder washing * |
| 5 | The recommended antibiotic therapy is active against group B streptococci. | Organism Candida and upper tract, then recommend amphotericin B IV, fluconazole IV, consult. |

FIG. 14

TABLE 8 (Duration Rules (Optionally Sequential))

| | | |
|---|---|---|
| 1 | 14 days. | Infection upper tract or early recurrence or suprapubic catheter |
| 2 | 1 day. | Organism is chlamydia and (pregnant or age <8) then recommend 1 day duration. |
| 3 | 3 days. | Infection lower tract and outpatient and no duration factors (table: "duration factors") present and recommended therapy is (FQ or TMP/SMX) and ((urine collection clean catch and is not culture negative and organism is not GPC, GPR, chlamydia, Pseudomonas aeruginosa, Candida) or (urine collection method is "none collected")) |
| 4 | 7 days | Recommend 7 days duration |

FIG. 15

TABLE 9 (One or more optional Caveats)

| | | |
|---|---|---|
| 1 | Remove Foley catheter if possible. | Urine collection method Foley catheter |
| 2 | If catheter not removed, treat for 14 days. | Urine collection method Foley catheter and (lower tract infection or asymptomatic) |
| 3 | If clinical response is satisfactory after 2–3 days and GI absorption is adequate, therapy may be switched to oral agent based on organism identification and susceptibility. | Inpatients and upper tract infection |
| 4 | Collect urine specimen. | Urine collection none (and infection is upper tract or any duration factors present) |
| 5 | Collect urine specimen if clinical response unsatisfactory. | Urine collection none (and infection is not upper tract and no duration factors present) |
| 6 | Assumes urine microscopic exam shows WBCs. If sexually active, recommend evaluation for Chlamydia trachomatis and Neisseria gonorrhoeae. | Organism uncertain and culture is negative and urine collection is clean catch and therapy is outpatient and infection is lower tract |
| 7 | Sexual partners should be referred for evaluation and treatment. | Organism chlamydia |
| 8 | This organism is associated with encrusted cystitis and pyelitis. | Organism corynebacterium |
| 9 | Confirm isolated enterococcus is sensitive to ampicillin. | Organism Enterococcus is resistant to vancomycin and is not resistant to ampicillin |
| 10 | Recommend repeat culture prior to starting antibiotics. | Three organisms identified |

FIG. 16

TABLE 10 (Mitigating Factors)

| # | Factor |
|---|---|
| 1 | If pregnant, query "Near term?" |
| 2 | If penicillin allergy, query "Was penicillin allergy immediate-type" |

FIG. 17

TABLE 11 (Sequentuial Mitigating Factors)

| # | Rule |
|---|---|
| 1 | If not upper tract and not ((suprapubic or nephrostomy) and lower tract), then query "Early relapse or recurrence?" and "Urinary obstruction or abnormal urologic anatomy?" |
| 2 | If female and not pregnant and clean catch and lower tract and age 15-50 and (organism uncertain or GNR not identified to species or E. coli), then query duration factors |
| 3 | If organism Staph coagulase negative or (organism uncertain and upper tract), then query urinary obstruction, abnormal urologic anatomy, recent urologic surgery |
| 4 | If asymptomatic and not pregnant and (organism not chlamydia or Salmonella) and age > 3, then query "Early post-renal transplant period?" and "Urinary obstruction or recent/planned urologic surgery?" |

FIG. 18

TABLE 12 (Contraindictions)

| Medication | Contraindication |
|---|---|
| Penicillin | Penicillin allergy<br>Imipenem allergy<br>Cephalsporin allergy<br>Penicillin resistance<br>Cephalsporin resistance |
| Nafcilling, Dicloxacillin and Oxacillin | Penicillin allergy<br>Imipenem allergy<br>Oxacillin resistance |
| TMP/SMX | TMP/SMX or Sulfa alergy<br>Nursing female<br>Pregnant female near term<br>TMP/SMX resistance |
| Cephalosporin | Immediate penicillin allergy<br>Cephalsporin allergy<br>Cephalsporin resistance<br>Oxacillin resistance |
| Imipenem | Penicillin allergy<br>Imipenem allergy<br>Imipenem resistance<br>History of seizure activity |
| Tetracyclines | Tetracyclines allergy<br>Tetracyclines resistance<br>Pregnancy<br>Nursing<br>Age < 8 years |
| FQ | Pregnancy<br>Nursing<br>Age < 18 years<br>FQ resistance<br>FQ allergy |
| Erythromycin estolate | Pregnancy |

FIG. 19

TABLE 13 (Meningitis Anti-bacterial Antibiotic Selection Rules and Statements)

| # | Statement | Rule |
|---|---|---|
| 1 | Broad empiric coverage which accounts for *Listeria* and gram-negative rods, as well as common gram-positive and gram-negative cocci (including DRSP) | If organism uncertain and patient has depressed cellular immunity OR age 1 month to 3 months), then: ($3^{rd}$ gen ceph + ampicillin + vancomycin), ($3^{rd}$ gen ceph + vancomycin), meropenem, chloramphenicol |
| 2 | Broad empiric coverage for common organisms, with coverage for DRSP and gram-negatives | If organism uncertain and age>3 months, then (Vanco +$3^{rd}$ gen ceph), Meropenem |
| 3 | Broad empiric coverage aimed toward Group B Strep, *E. coli*, and *Listeria* | If organism uncertain and AGE (preterm to 1 month) then: (Amp + Cefotax), (Amp + Gent) |
| 4 | Empiric coverage primarily against *S. pneumoniae*. Initial coverage with Vanco is preferred to cover for DRSP, as well as MRSA or MRSE if clinically appropriate. | If GRAM-STAIN GRAM-POS COCCI, then ($3^{rd}$ Gen Ceph + Vanco), (Vanco + Rif), $3^{rd}$ Gen Ceph, chloramphenicol |
| 5 | Empiric therapy primarily for *N. meningitidis* | If GRAM-STAIN GRAM-NEG COCCI then: $3^{rd}$ Gen Ceph, Chloramphenicol |
| 6 | Empiric therapy primarily for *Listeria* | If GRAM-STAIN GRAM-POS BACILLI then: (Amp + Gent), TMP/SMX |
| 7 | Empiric therapy for gram-negative rods, with particular attention to *H. influenzae*, coliforms, and *P. aeruginosa* | If GRAM-STAIN GRAM-NEG BACILLI then: Meropenem, ceftazidime |
| 8 | Recommended therapy is active against methicillin-resistant *S. aureus* and *S. epidermidis* (MRSA, MRSE) | If (organism *S. aureus* or organism *Staphylococcus* coagulase negative) and oxacillin resistant, then (vancomycin + rifampin), vancomycin, |

FIG. 21A

TABLE 13 (Meningitis Anti-bacterial Antibiotic Selection Rules and Statements)

| # | Statement | Rule |
|---|---|---|
| 9 | Recommended therapy is active against methicillin-sensitive S. aureus and S. epidermidis | If organism (S. aureus or Staphylococcus coagulase negative) and oxacillin susceptible and CNS shunt present (?), then (nafcillin + rifampin), nafcillin, (vancomycin + rifampin), vancomcyin (should CNS shunt be in #9?) |
| 10 | Recommended therapy is active against S. aureus and S. epidermidis. Vancomycin is preferred when the rate of methicillin resistance exceeds 10% | If (organism S. aureus or Staphylococcus coagulase negative) and susceptibility unknown, Vancomycin, nafcillin |
| 11 | Recommended therapy is active against S. pneumoniae sensitive to penicillin or $3^{rd}$ Gen Ceph | If organism S. pneumoniae (Pen MIC <0.1 or Ceftriaxone MIC$\leq$0.5 ug/ml), then $3^{rd}$ Gen Ceph, (Vanco + Rif) |
| 12 | Recommended therapy is active against S. pneumoniae which has intermediate resistance to $3^{rd}$ Gen Ceph. It is also recommended as empiric therapy for S. pneumoniae when susceptibility is not known. | If organism S. pneumoniae and (susceptibility unknown or Ceftriaxone MIC>0.5 ug/ml) then: ($3^{rd}$ Gen Ceph + Vanco), (Vanco + Rif), Chloramphenicol |
| 13 | Recommended therapy is active against S. pneumoniae resistant to penicillin and ceftriaxone. A $3^{rd}$ Gen Ceph is recommended as it may still provide some in vivo activity. | If organism S. pneumoniae and Ceftriaxone MIC$\geq$2 ug/ml) then: ($3^{rd}$ Gen Ceph + Vanco + Rif), (Vanco + Rif), Chloramphenicol |
| 14 | Recommended therapy is active against S. agalactiae | If organism S. agalactiae, then (Amp + Gent), (Ceftriax or Cefotax), Vanco |
| 15 | Recommended therapy is active against N. meningitidis | If organism N. meningitidis then: $3^{rd}$ gen ceph, Chloramphenicol |

FIG. 21B

TABLE 13 (Meningitis Anti-bacterial Antibiotic Selection Rules and Statements)

| # | Statement | Rule |
|---|-----------|------|
| 16 | Recommended therapy is active against *L. monocytogenes* | If organism *L. monocytogenes* then: (Amp + Gent), ampicillin, TMP/SMX |
| 17 | Recommended therapy is active against *H. influenzae* | If organism *H. influenzae* then: $3^{rd}$ gen ceph, chloramphenicol |
| 18 | Recommended therapy is active against gram-negative rods, with particular attention to *H. influenzae*, coliforms, and *P. aeruginosa* | If organism gram negative rod then: meropenem, intrathecal gentamicin |
| 19 | Recommended therapy is active against *P. acnes* | If organism is *Propionibacterium acnes*, then penicillin G, chloramphenicol |

FIG. 21C

TABLE 14 (Duration Rules)

1. If organism is gram negative rod or listeria then state "Recommended duration of antibiotic therapy is 3 weeks"
2. If organism is *H. influenzae* or *N. meningitidis,* state "Recommended duration of antibiotic therapy is 7 days"
3. If organism is *S. aureus* or Staphylococcus coagulase negative or *S. agalactiae,* state "Recommended duration is 14 – 21 days"
4. If organism is *S. pneumoniae,* state "Recommended duration is 10-14 days"

FIG. 22

TABLE 15 (Mitigating Factor Rules)

1. If organism is uncertain, then query "Does patient have depressed cellular immunity (HIV infection, organ transplantation, chronic steroid use)?"

2. Query if CNS shunt present

FIG. 23

TABLE 16 (Caveats)

1. If CNS shunt present, then state "Removal of shunt probably necessary for cure"

2. State "Recommendations for treatment duration are general guidelines; treatment should be tailored to the individual's response"

3. In cases of proven or strongly suspected bacterial meningitis, dexamethasone should be given at the time of the first dose of antibiotic, particularly when there are signs of increased intracranial pressure.

4. If organism gram negative rod and not *H. influenzae*, then state "Intrathecal gentamicin may be considered in the event of poor clinical response to intravenous antibiotics"

5. If organism is *Listeria* or *S. agalactiae*, state "Gentamicin may be stopped after 5 to 7 days of therapy if the clinical response is adequate"

FIG. 24

SYSTEMS AND METHODS FOR MANIPULATING MEDICAL DATA VIA A DECISION SUPPORT SYSTEM

CROSS-REFERENCE TO RELATED APPLICATIONS

This application is a divisional of application Ser. No. 09/666,429, filed on Sep. 21, 2000 now abandoned, which is incorporated herein by reference.

BACKGROUND OF THE INVENTION

1. The Field of the Invention

This invention relates to a decision-support system where information is analyzed to provide an individual with one or more suggested recommendations. More specifically, the present invention relates to a decision-supporting system that provides recommendations to a clinician in a standardized and reproducible form.

2. The Relevant Technology

The U.S. health care delivery system has undergone breathtaking changes since the late 1980's. Today's medical marketplace is characterized by escalating costs, diminishing resources, demands for accountability, inescapable conflicts regarding meaningful outcomes measures, and an expanding medical knowledge base. Health care, in general, is an information intensive industry where clinicians and health care providers analyze and digest an ever-increasing knowledge base of health care practices and procedures. Clinicians and health care providers use these practices and procedures to give appropriate medical care for each patient that seeks medical care.

Increasingly clinicians and health care researchers experience demands for more accurate and accessible information. The complexity of health care, its burgeoning information base, and the turbulence of the medical marketplace contribute to a medical system that grapples to efficiently synthesize and disseminate information, standardize care, and to continue to create and innovate. The obstacles to these goals are the same regardless of whether the health care delivery provider is a small hospital, long-term/skilled nursing facility, medical clinic, home health agency, hospice, emergent care unit, or large institution. All providers are faced with the need to identify solutions to manage information and make better decisions, whether those decisions are medical or business-related in nature.

Clinical decisions are of particular interest since they often influence the balance of human suffering and well-being. Clinical decisions are typically based upon the evidence-base of medicine, patient-physician factors and interactions, and external and internal constraints. Whether clinicians are serving individual patients or populations, they have always sought to base their decisions on the best available evidence or knowledge. The rapid expansion of the scientific and clinical evidence has changed the health care landscape so that no longer is the question how much of medical practice is based in evidence, but rather how much of the available evidence is applied at the front lines of patient care.

Clinicians and health care providers are acutely aware of the issues associated with practicing the available evidence at the front lines. Many attempts have been made to provide information to a clinician in a meaningful manner that supports the clinician's decision-making process. One current trend is to utilize artificial intelligence (AI) technologies to meet information management and decision-supporting needs. AI technologies or expert systems attempt to simulate the decision-support process that is easily accomplished by the human brain. The expert system typically includes a knowledge base that stores data representative of the currently available knowledge within a particular field of endeavor. An inference engine and associated "rules" or statements that control how the expert system reacts to a particular situations work with the knowledge base to generate solutions to problems posed to the expert system, such as the dose of a drug that a patient is to receive.

Various types of expert system have been developed in the medical field. For example, one type of expert system aids a physician with treating physical trauma. The expert system gathers patient data, such as the patient's height, weight, age, and sex, while collecting information related to the physical trauma. As the data is collected, the expert system generates a working file that is specific to the patient and the particular injury. This working file with a knowledge base of physical trauma and orthopedic fractures is used by the expert system to assist the clinician in treating the patient's physical trauma. Unfortunately, each working file is specific to the particular patient and the specific injury. Hence, each time the expert system is used, a new working file is generated, including the need to ask for patient data, patient history, and the like.

Another type of expert system guides a clinician with the administration and selection of therapeutic drugs and associated treatment regimens for a known disease. The expert system utilizes information gathered from a patient physical examination with a knowledge base to generate suggested treatment regimens for a known disease or medical condition. Although this type of expert system allows a clinician and a patient to generate treatment regimens together for a known disease, the expert system is limited to only those known diseases identified by the clinician. Additionally, initial generation of patient data is time consuming and cumbersome.

Therefore, there is a need for an expert system that allows for an evaluation of a patient over an extended period without the need to re-input patient data each time a clinician examines the same patient. Additionally, there is a need for a system that effectively gathers patient data without the clinician spending a long period examining the patient and evaluates the data to identify known or unknown medical conditions.

BRIEF SUMMARY OF THE INVENTION

It is an object of the present invention to provide a system and method for accessing medical information in an efficient and controllable manner.

It is another object of the present invention to provide a system and method for presenting a clinician with medical information in a standardized manner and reproducible form.

Another object of the present invention is to provide a system and method that conveys medical information in a concise manner that aids a clinician in diagnosing and treating medical conditions.

Yet another object of the present invention is to provide a system and method for allowing a patient to provide medical information on themselves and their relatives in a controlled and simple manner.

Still yet another object of the present invention is to provide a system and method for generating one or more questions specific to a patient based upon the patient's responses to previous medical related questions.

Still yet another object of the present invention is to provide a system and method for generating a decision-supported progress note that provides the clinician with guidance as to potential medical conditions of a patient.

Still yet another object of the present invention is to provide a system and method to allow real-time communication between a decision supporting system and a clinician to aid the clinician in making informed decisions related to patient medical care.

Another object of the present invention is to provide systems and methods for collecting patient and family histories of medical conditions and genetic predispositions to determine and infer a patient's long-term risk Still another object of the present invention is to provide systems and methods for using pharmacogenomic data to determine the medical treatment prescribed to a patient.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims. These and other objects of the present invention will become more fully apparent from the following description and appended claims, or may be learned by the practice of the invention as set forth hereinafter.

As disclosed previously, clinicians are influenced by a number of complex and varied constraints as a clinician gives medical care to multiple patients each having varied medical conditions. Constraints on the time that a clinician may spend consulting with each patient limit the clinician's effectiveness in diagnosing and treating each patient. Furthermore, although clinicians educate themselves with the advances in medical care, during the rigors of performing medical care for a large number of patients such knowledge may not raise to the clinician's memory. This may result in a misdiagnosis, mistreatment, or at worst the death of the patient. To achieve the foregoing objects, and in accordance with the invention as embodied and broadly described herein, systems and methods for providing clinicians with patient specific data and at least one medical diagnosis and at least one medical care recommendation that are based upon a large expert knowledge base are disclosed.

One of the modules implemented by one embodiment of the present invention is a decision-support module. The decision-support module is configured to generate decision-supported patient data that may be accessed by a user module via a network. The decision-supported patient data may optionally be contained within one or more files, records, fields or data storages termed a decision-supported progress note specific to each patient.

The decision-supported patient data represents patient specific information and data that have been evaluated by a knowledge base of expert medical knowledge, resulting in a diagnosis of a patient's medical condition and a medical care recommendation. Each decision-supported progress note, therefore, includes data representative of at least one medical condition and at least one medical care recommendation for a patient. Additionally, the decision-supported progress note provides a qualitative and quantitative analysis of the patient assessment process performed by the decision-support module and the clinician and the recommended plan of medical care suggested by the decision-support module over a short or long time period.

Another one of the modules implemented by one embodiment of the present invention is a user module. The user module communicates with the decision-support module by way of a web browser to act as an interface between the decision-support module and the clinician. In this manner, the clinician is presented with decision-supported patient data (such as in the form of the decision-supported progress note) through the web browser that gives the clinician an efficient and effective representation of the current medical condition of the patient.

The user module, either solely or in combination with the decision-support module, may generate a summarized version of the decision-supported patient data to assist the clinician in treating each patient that the clinician is to examine. The summarized version presents the clinician with the pertinent medical information associated with the patient's previous, existing, and any anticipated medical conditions.

According to another aspect of the present invention, in a decision-support system having data stored in a knowledge base, a method for delivering decision-supported patient data to a clinician to aid the clinician with the diagnosis and treatment of a medical condition is disclosed. The method optionally includes gathering patient data from a patient in response to a decision-supported questionnaire. The questionnaire includes a number of questions and decision-supported questions aimed at the patient. Alternatively, patient data may be gathered from one or more data storage modules or other databases.

Upon gathering the patient data, the method provides for the patient data to be evaluated with expert data stored in a knowledge base to generate decision-supported patient data. The evaluating step may include collecting medical condition information based upon the patient data. Once the medical condition is identified, the clinical classification of the medical condition is collected. Subsequently, data representative of one or more causes of the medical condition is collected. This data may be used to identify the microbial susceptibilities to the medical condition if the one or more causes of the medical condition are organism specific. Alternatively, mitigating factors based on the one or more causes of the medical condition are collected. Consequently, the medical condition identified is evaluated to generate the decision-supported patient data that includes at least one medical condition and at least one medical care recommendation.

Following generation of the medical condition and the medical care recommendation, the decision-supported patient data is transmitted to a user module in the form of a decision-supported progress note. The user modules present the clinician with the decision-supported patient data specific to the patient in a format that assists the clinician in treating each patient.

In this manner, the present invention is capable of receiving patient data, optionally directly from the patient and generating decision-supported patient data that assists a clinician in making decisions related to the medical care of a patient.

Similarly, by generating data on a patient's relatives, the present invention is capable of generating decision-supported data that assists a clinician in making decisions related to the medical care of a patient and furthermore in making decisions related to the medical care of one or more of the patient's relatives.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6A–6E illustrate Table 1 that contains statements that may be presented to the clinician and the underlying rules used by an inference module to generate the statements for the medical condition of Pneumonia;

FIG. 7 illustrates Table 2 that contains mitigating factor rules used by an inference module for the medical condition of Pneumonia;

FIG. 8 illustrates Table 3 that contains susceptibility rules used by an inference module for the medical condition of Pneumonia FIG. 9 illustrates Table 4 that contains duration rules used by an inference module for the medical condition of Pneumonia FIG. 10 illustrates Table 5 that contains caveat rules used by an inference module for the medical condition of Pneumonia

FIG. 12A–B is a schematic block diagram illustrating the various etiologic classifications for a Urinary Tract Infection that may be presented to the clinician in accordance with the teaching of the present invention;

FIG. 13A–F illustrates Table 6 that contains statements that may be presented to the clinician and the underlying rules used by an inference module to generate the statements for the medical condition of a Urinary Tract Infection;

FIG. 14 illustrates Table 7 that contains statements that the present invention may present to the clinician and the underlying rules used by an inference module to generate the statements for a *Candida* medical condition and other miscellaneous organism associated with a Urinary Tract Infection;

FIG. 15 illustrates Table 8 that contains duration rules and statements associated with the medical condition of a Urinary Tract Infection;

FIG. 16 illustrates Table 9 that contains caveat rules and statements associated with the medical condition of a Urinary Tract Infection;

FIG. 17 illustrates Table 10 that contains mitigating factor rules and statements associated with the medical condition of a Urinary Tract Infection;

FIG. 18 illustrates Table 11 that contains sequential mitigating factor rules and statements associated with the medical condition of a Urinary Tract Infection;

FIG. 19 illustrates Table 12 that contains illustrative medication contraindications for the medical condition of a Urinary Tract Infection;

FIG. 21A–C illustrates Table 13 that contains statements that the present invention may presented to the clinician and the underlying rules used by an inference module to generate the statements for the medical condition of Meningitis;

FIG. 22 illustrates Table 14 that contains duration rules associated with the medical condition of Meningitis;

FIG. 23 illustrates Table 15 that contains mitigating factor rules associated with the medical condition of Meningitis; and FIG. 24 illustrates Table 16 that contains caveat rules associated with the medical condition of Meningitis.

DETAILED DESCRIPTION OF THE PREFERRED EMBODIMENTS

The present invention extends to both methods and systems for delivering decision-supported patient data to a clinician to aid the clinician with the diagnosis and treatment of a medical condition. The embodiments of the present invention may comprise a special purpose or general purpose computer including various other computer hardware and/or software modules and components, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

Figure 1:
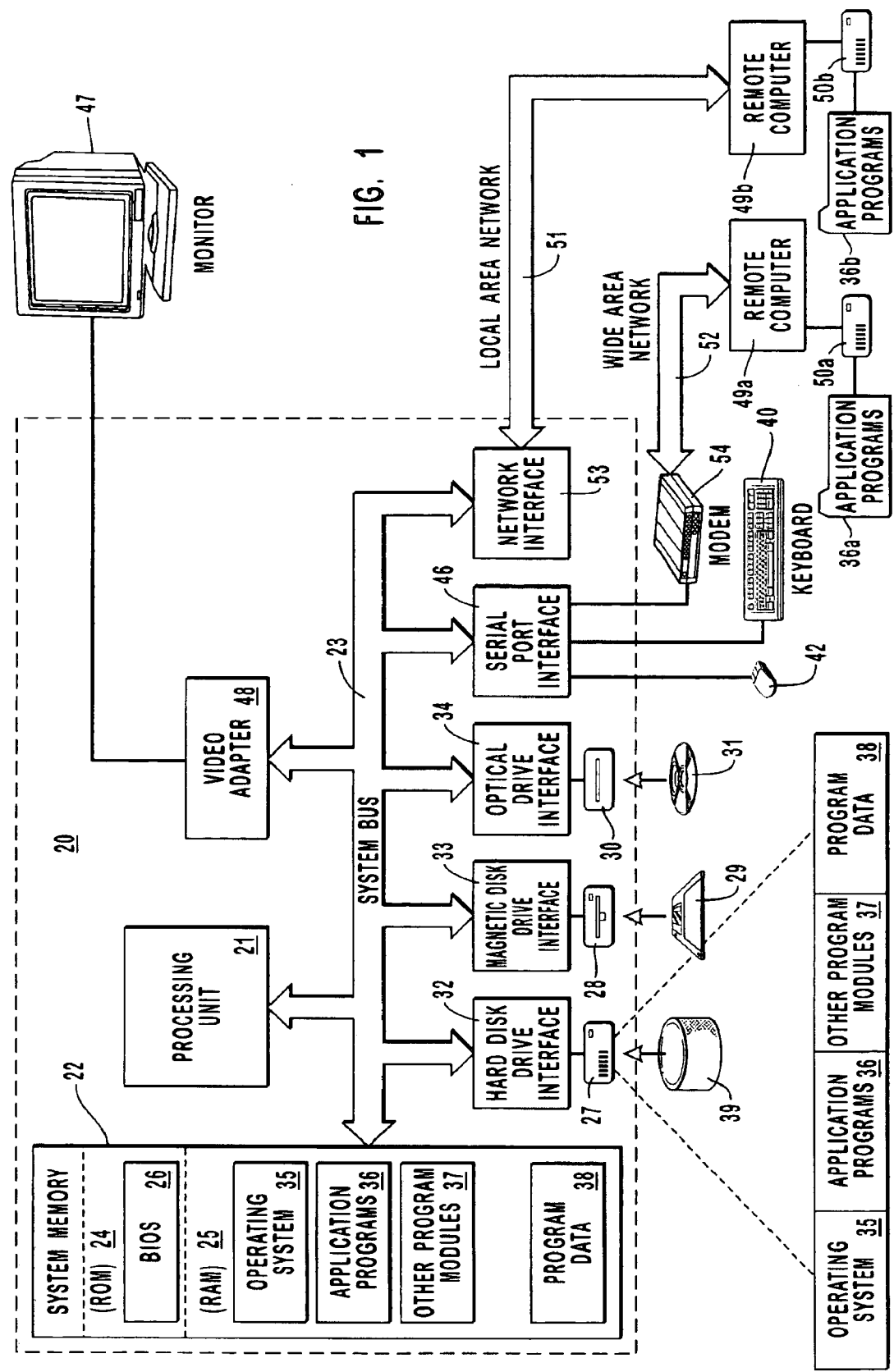
FIG. 1 illustrates an exemplary system that provides a suitable operating environment for the present invention.

FIG. 1 and the following discussion are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 1, an exemplary system for implementing the invention includes a general purpose computing device in the form of a conventional computer 20, including a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help transfer information between elements within the computer 20, such as during start-up, may be stored in ROM 24.

The computer 20 may also include a magnetic hard disk drive 27 for reading from and writing to a magnetic hard disk 39, a magnetic disk drive 28 for reading from or writing to a removable magnetic disk 29, and an optical disk drive 30 for reading from or writing to removable optical disk 31 such as a CD-ROM or other optical media. The magnetic hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer-executable instructions, data structures, program modules and other data for the computer 20. Although the exemplary environment described herein employs a magnetic hard disk 39, a removable magnetic disk 29 and a removable optical disk 31, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 39, magnetic disk 29, optical disk 31, ROM 24 or RAM 25, including an operating system 35, one or more application programs 36, other program modules 37, and program data 38. A user may enter commands and information into the computer 20 through keyboard 40, pointing device 42, or other input devices (not shown), such as a microphone, joy stick, game pad, satellite dish, scanner, or the like. These and other input devices are often connected to the processing unit 21 through a serial port interface 46 coupled to system bus 23. Alternatively, the input devices may be connected by other interfaces, such as a parallel port, a game port or a universal serial bus (USB). A monitor 47 or another display device is also connected to system bus 23 via an interface, such as video adapter 48. In addition to the monitor, personal computers typically include other peripheral output devices (not shown), such as speakers and printers.

The computer 20 may operate in a networked environment using logical connections to one or more remote computers, such as remote computers 49a and 49b. Remote computers 49a and 49b may each be another personal computer, a server, a router, a network PC, a peer device or other common network node, and typically includes many or all of the elements described above relative to the computer 20, although only memory storage devices 50a and 50b and their associated application programs 36a and 36b have been illustrated in FIG. 1. The logical connections depicted in FIG. 1 include a local area network (LAN) 51 and a wide area network (WAN) 52 that are presented here by way of example and not limitation. Such networking environments are commonplace in office-wide or enterprise-wide computer networks, intranets and the Internet.

When used in a LAN networking environment, the computer 20 is connected to the local network 51 through a network interface or adapter 53. When used in a WAN networking environment, the computer 20 may include a modem 54, a wireless link, or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing communications over wide area network 52 may be used.

Figure 2:
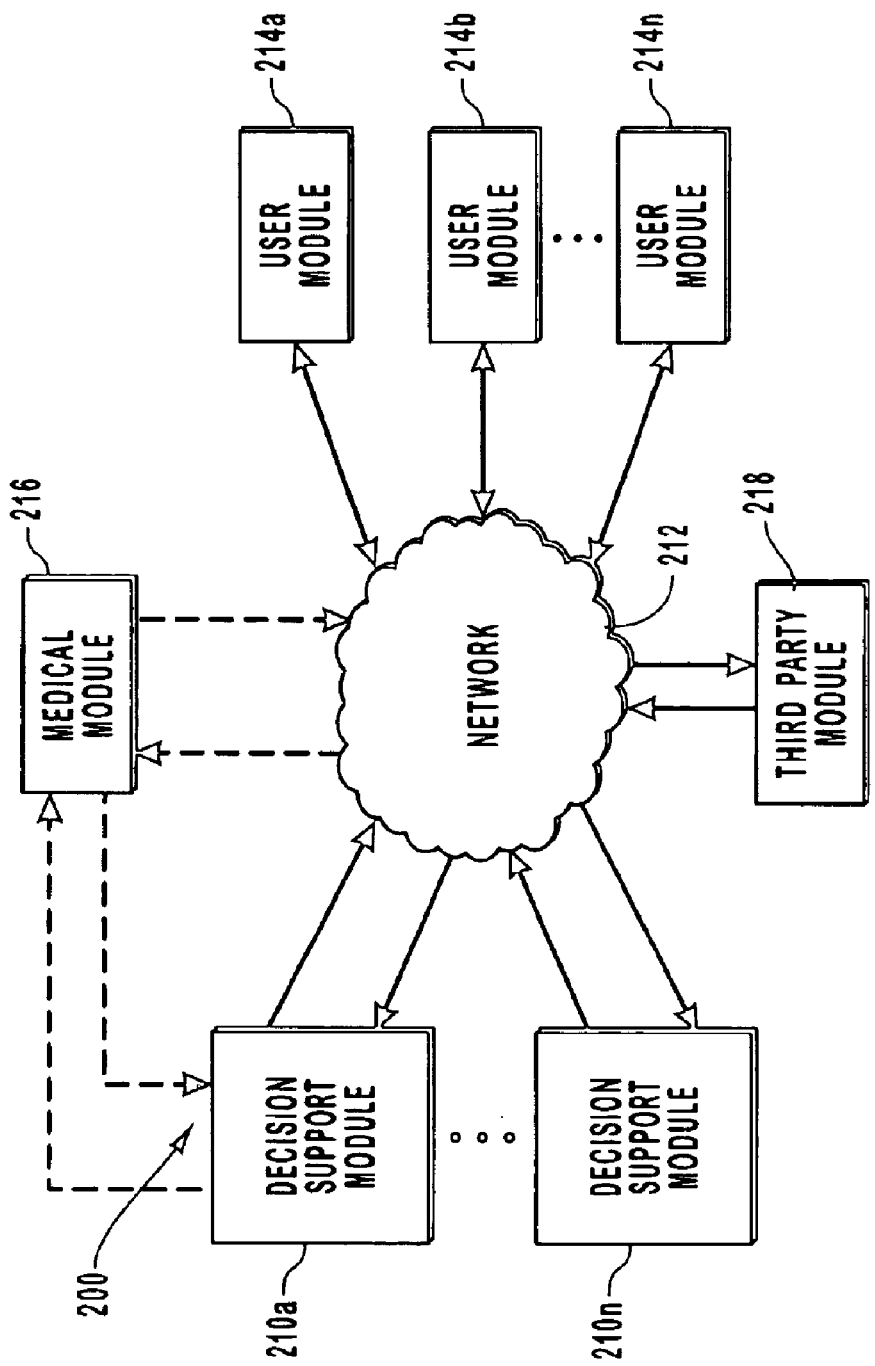
FIG. 2 is a schematic representation of one embodiment of the system of the present invention.

FIG. 2 is a block diagram illustrating a decision support system implementing one embodiment of the present invention. As shown, system 200 includes a decision-support module 210 that communicates with one or more user modules 214a–214n via network 212. Alternatively, system 200 may include multiple decision-support modules that communicate with a single user module. Through the configuration illustrated in FIG. 2, a patient or clinician may input information regarding the patient's health, medical conditions, billing information, and past and current medical care, termed "patient data". Subsequently, system 200 may evaluate this patient data to create data that assists the clinician in making a medical diagnosis, a medical care recommendation or decision, medical treatment, a referral to another clinician or medical provider, or the like. Such data is termed "decision-supported patient data."

Optionally, the decision-supported patient data may be configured in the form of a decision-supported progress note. The decision-supported progress note is a module, data file, record, field, one or more data storages that contain information and data that represents a qualitative and quantitative analysis of the patient assessment process performed by the decision-support module 210 and the clinician and the recommended plan of medical care suggested by decision-support module 210. Such qualitative and quantitative analysis may extend over a long period, such as with an outpatient situation, or over a shorter period, such as with an inpatient situation.

In this manner, system 200 may gather and analyze stored patient data with input patient data to generate decision-supported patient data, optionally, in real-time or perceived real time. Although discussion is made to the use of the present invention in a decision-support system, it may be appreciated that the novel features of the present invention are not limited to use with a decision-support system, but may be used in various other systems.

As illustrated in FIG. 2, system 200 includes decision-support module 210. Decision-support system 210, in one embodiment, allows a patient to store and access patient data, while allowing a clinician to store, update, and access the patient data and decision-supported patient data that contain information regarding the diagnosis and treatment of various medical conditions. Additionally, the clinician may access a knowledge base that includes data representative of the current expert medical knowledge within a variety of medial areas and assists the clinician with the diagnosis and medical care of the patient. The patient data, the decision-supported patient data, and the knowledge base need not be incorporated within decision-support module 210, but may be located remotely from decision-support module 210 and accessible by decision-support module 210. For example, optional medical module 216, as illustrated by dotted lines, may include one or more servers that store the patient data, the decision-supported patient data, and the knowledge base.

Facilitating communication between decision-support module 210, user modules 214a–214n, and optionally medical module 216 is network 212. In one embodiment, network 212 is the Internet so that various user modules 214a–214n using web browsers may access the patient data, decision-supported patient data, and decision-supported progress notes stored within decision-support module 210. Network 212 may also be a local area network (LAN) such as a hospital or clinic intranet, wide area network (WAN), wireless network, packetized network, real-time network, and various other networks known by one skilled in the art, so long as the network configuration and architecture allow a user module to access decision-support module 210.

Decision-support module 210 may communicate with user modules 214a–214n via various types of communication line connections, such as but not limited to, cable or cable modems, satellite, telephone lines, whether analog or digitally based, the Internet, DSL, G-Lite, wireless technology, infra-red (IR) technology, other high-speed data connections, or any other suitable transmission technology or medium. One skilled in the art may identify various other types of network and/or communication line connections that are capable of performing the desired function of allowing decision-support module 210 to communicate with user modules 214a–214n and optionally medical module 216.

Each user module 214a–214n communicates with decision-support module 210 to allow the clinician or patient to gather patient data and receive decision-supported patient data or the decision-supported progress note in real-time or perceived real-time. As discussed herein, the operation of either transmitting data and/or receiving data, in various forms and types, shall be termed collectively as "transceiving" and the operation of tranceiveing data between decision-support module 210, user module 214a–214n, and medical module 216 without a substantial delay between an input and a response is considered real-time or perceived real-time communication.

Those skilled in the art will appreciate that each user module 214a–214n may take various configurations. For example, each user module 214a–214n may be the same or different personal computer, hand-held device, multi-processor system, microprocessor-based or programmable consumer electronic device, telephone, network PC, minicomputer, mainframe computer, and the like. Generally, each user module 214a–214n may include the structure and functionality of computer 20 with associated application programs 36 and memory 22 to store the application programs 36, patient data, decision-supported patient data, and optional decision-supported progress note.

Medical module 216 represents the various hardware and software modules and components of a medical facility, such as a hospital, clinic, and the like. Each medical facility may store business data, medical data, patient data, decision-supported patient data, decision-supported progress notes, and the like. Medical module 216, in one embodiment, includes various modules associated with the medical facility's intranet or internal network that links various departments of a hospital or clinic. For example, the departments may include radiology, the pharmacy, administration, the laboratories, and the like. Additionally, medical module 216 may include the hardware and software modules and components for medical module 216 to communicate with decision-support module 210 and user modules 214a–214n by a communication line connection known to one skilled in the art in light of the teaching contained herein.

According to another aspect of the present invention, system 200 optionally includes a third party module 218. Third party module 218 represents the various other modules that may communicate with decision-support module 210, user modules 214a–214n, and medical module 216. For example, third party module 218 may represent a medical provider, an insurance carrier, a referred clinician, a referring clinician, a third party paging service, and the like. In this manner, a clinician may communicate with outside sources to obtain approval for services and/or give information to the outside sources. For example, system 200 may allow decision-support module 210 to communicate with an insurance carrier, heath care management organization (HMO), or other similar health care provider to receive authority to give a recommended medical treatment. One skilled in the art may identify various other third parties that may obtain benefits from the present invention.

Generally, the configuration of system 200 facilitates the gathering of patient data and delivery of decision-supported patient data to a clinician and patient. Optionally, system 200 may present the clinician or patient with a summarized version of the available medical and non-medical information via user module 214a–214n. Such medical and non-medical information provides the clinician and the patient with recommendations regarding the patient's care and may include warnings or alerts with respect to recommended treatments or potential medical conditions of the patient. For example, the alerts may identify potential side effects associated with the use of the medication.

By summarizing the decision-support patient data, the clinician is not bombarded with a large quantity of information through which he or she must search. Rather, the clinician may view the current decision-supported patient data, i.e., recent laboratory test results, vital statistics, current drug usage, and the like. In this fashion, the clinician is given a simplified representation of the patient's medical condition based upon the current medical knowledge and the current patient data. Thus, medical costs are reduced and a higher quality of medical care is provided to each patient.

Furthermore, the configuration of system 200 facilitates the delivery of patient data to the clinician in a standardized and reproducible manner. The clinician may request real-time patient data from decision-support module 210, medical module 216, or third-party module 218 on demand and receive the patient data in a standardized format. Such patient data may be delivered to the clinician via user module 214a–214n and displayed to the clinician through a browser or other user interface. Additionally, the configuration of system 200 facilites the delivery of important or critical information and patient data to the clinician, whether in a synchronized basis or upon the occurrence of an alerted event, such as when a patient has heart attack or an adverse reaction to prescribed medication.

Generally, each of the modules, 210, 214a–214n, 216, and 218 may be incorporated within various types of computer 20 and remote computers 49a, 49b as depicted in FIG. 1. Each module 210, 214a–214n, 216, and 218, therefore, may include system memory 22 and storage devices 50a and 50b, while optionally including hard disk drive 27, magnetic disk drive 28, optical disk drive 30, and associated interfaces 32, 33, and 34. Additionally, each module 210, 214a–214n, 216, and 218 may communicate one with another via a variety of different manners and communication line connections. Hence, the functionality of each module 210, 214a–214n, 216, and 218 may be incorporated within one or more of the other modules. For example, the functionality of decision-support module 210 and/or of user modules 214a–214n may be incorporated within medical module 216.

Figure 3:
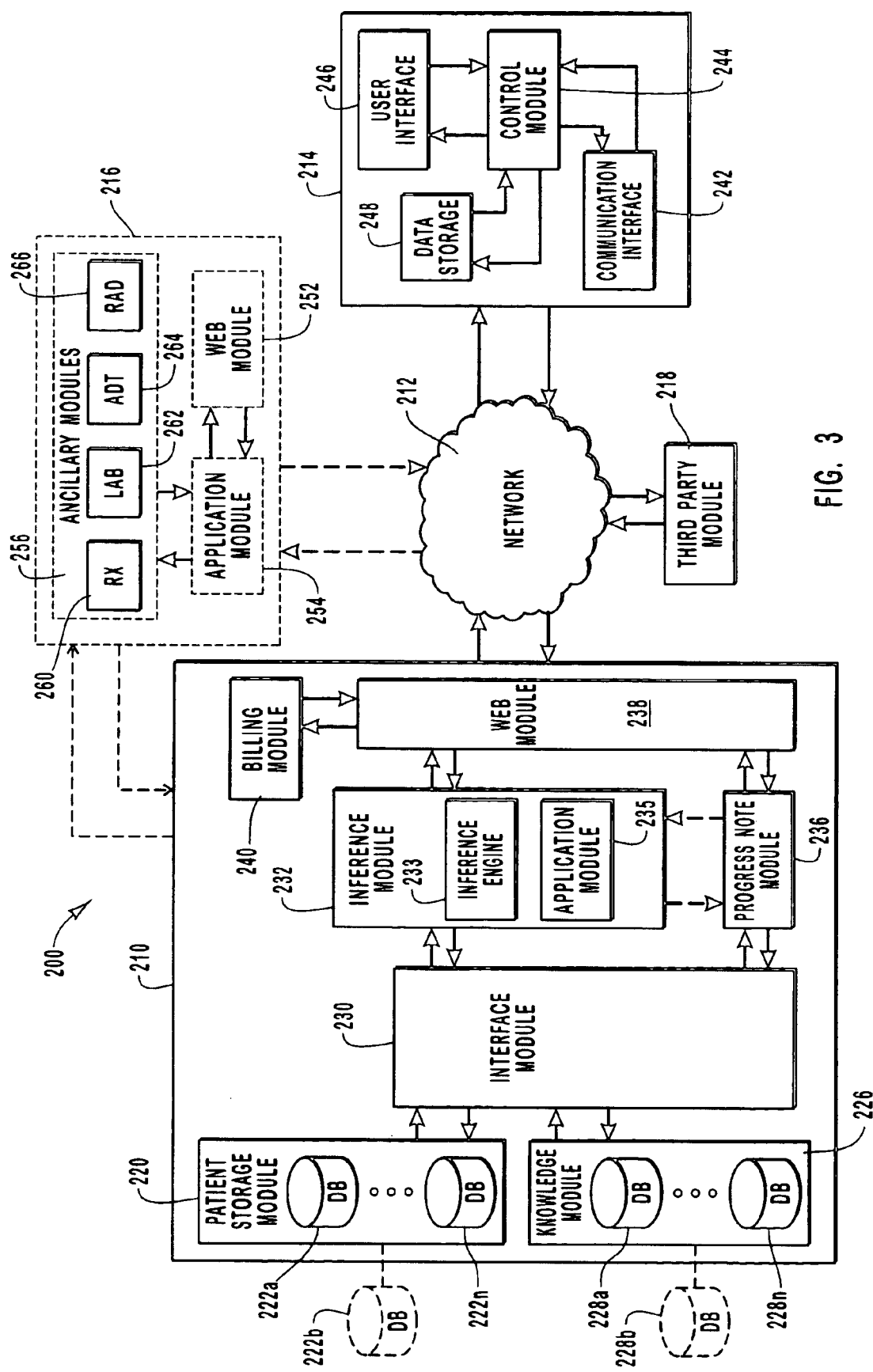
FIG. 3 is a more detailed a schematic representation of the system of FIG. 2.

With reference to the more detailed schematic representation of one embodiment of the present invention depicted in FIG. 3, only a single decision-support module 210 and a single user module 214 are depicted. The following discussion will relate to the interaction between one decision-support module 210 and one user module 214. One skilled in the art may appreciate, however, that a similar discussion may be recited for the interaction of multiple decision-support modules and multiple user modules.

According to one embodiment of the present invention decision-support module 210 includes a patient storage module 220. Patient storage module 220 stores the patient data that may be used by the clinician and decision-support module 210 to establish the type of medical care received by the patient. As illustrated, patient storage module 220 includes one or more databases 222a–222n that maintain the patient data. Each database 222a–222n may have various architectures, such as but not limited to, relational, network, flat, and hierarchical databases, with associated database management systems (not shown) that control the flow of data to and from databases 222a–222n. Although multiple databases are represented, one skilled in the art may appreciate that system 200 may include only a single database.

The patient data maintained in databases 222a–222n may include, but is not limited to, the patient's billing information (e.g., name, address, telephone number, birth data, social security number, and insurance information) and patient's demographic information (e.g., age, sex, height, and weight). Additionally, databases 222a–222n include the patient's past and current: (i) medical conditions; (ii) medical care; (iii) tracked cure and failure information; (iv) medications prescribed and associated adverse effects of drug interactions; (v) laboratory tests and results; (vi) clinical consequences of treatment; (vii) family histories; (viii) genetic susceptibilies and pharmacological and non-pharmacological information; (ix) decision-supported patient data and progress notes; (x) and the like. Such data may be stored in a variety of different fields, files, and records that are associated one with another to allow an appropriate database management system (not shown) to access the stored data in an efficient manner when requested by interface module 230.

In accordance with another aspect of the present invention, decision-support module 210 includes a knowledge module 226. Knowledge module 226, and associated databases 228a–228n, act as the repository of medical information, data, and associated rules and parameter descriptions i.e., "knowledge", which decision-support module 210 uses to identify an unknown medical condition of a patient or provide recommendations for treatment of the medical condition when the condition is known or unknown. The rules represent logic sectors or elements that act upon information gathered by system 200 to generate the decision-supported patient data and the decision-supported progress note. The rules are either sequential or non-sequentially followed to generate the medical care recommendations. Following hereinafter are a list of illustrative rules that system 200 may use to generate the decision-supported patient data and decision-supported progress note based upon stored and newly gathered patient data and/or patient data associated with the patient's relatives.

The medical information and data stored within knowledge module 226 are based on information from experts within the relevant fields of medicine, such as such as Geriatric Medicine, Genetic Medicine and Gene Therapy, Cardiovascular diseases, Respiratory diseases, and the like. Knowledge module 226, therefore, may include information related to, but not limited to, Critical Care Medicine, Renal diseases, Genitourinary diseases, Gastrointestinal diseases, Diseases of the liver, gallbladder, and bile ducts, Hematologic diseases, Oncology, Metabolic diseases, Nutritional diseases, Endocrine diseases, Women's Health, Diseases of bone and bone mineral metabolism, Diseases of the immune system, Musculoskeletal and connective tissue diseases, Infectious diseases, HIV and Acquired immunodeficiency syndrome, Diseases of protozoa and metazoa, Neurological Diseases, Eye, Ear, Nose, and Throat diseases, Skin diseases, Pediatric Medicine, and the like.

The rules and parameter descriptions stored in knowledge module 226 may include one or more software modules, files, and records that define how decision-support module 210 uses the expert information to analyze the patient's current medical information. In this manner, the clinician is guided with the identification and treatment of a patient's medical condition. Such rules and parameters are dynamic in that as system 200 gathers more "knowledge" the rules and parameters changes to accommodate the increased knowledge. This is in contrast to many existing expert systems that utilize hard coded rules and parameters that are difficult to vary based upon an increasing knowledge base. Illustrative rules and parameters related to Pneumonia, Meningitis, and Urinary tract Infection will be discussed hereinafter.

As with databases 222a–222n, each database 228a–228n may have various architectures, such as but not limited to, relational, network, flat, and hierarchical databases, with associated database management systems (not shown) that control the flow of data to and from databases 228a–228n. It may be appreciated that is preferable that databases 222a–222n and 228a–228n have the same architecture, however, each database 222a–222n and 228a–228n may have differing architectures.

Although FIG. 3 illustrates each database 222a–222n and 228a–228n as being incorporated within decision-support module 210, one skilled in the art may appreciate that such databases 222a–222n and 228a–228n and/or patient storage module 220 and knowledge module 226 may be remotely located from decision-support module 210. Alternatively, in one configuration, patient storage module 220 and/or databases 222a–222n may be incorporated within a hospital or clinic's administrative system and/or network (medical module 216) that allow decision-support module 210 to access the information stored therein. In another configuration, patient storage module 220 and/or databases 222a–222n are located remotely from decision-support module 210 and a hospital or clinic's administrative system and/or network (medical module 216).

Communicating with patient storage module 220 and/or knowledge module 226 is an interface module 230. Interface module 230 facilitates the decision-support process by providing access to databases 222a–222n and 228a–228n. Interface module 230, therefore, allows decision-support module 210 to obtain patient data from medical module 216. Such communication between interface module 230 and medical module 216 may be via a variety of communication protocols and communication line connections. In one illustrative embodiment, interface module 230 allows communication via the Health Level 7 protocol, via Extensible Markup Language (XML), or by some other communication protocol known by one skilled in the art in light of the teaching contained herein. As may be understood by one skilled in the art, interface module 230 may be generated by a variety of different software tool and products, such as but not limited to Enterprise Java Beans (EJB), Common Object Request Broker Architecture (COBRA), and Common Object Model (COM) compliant services, and the like.

Communicating with interface module 230 is inference module 232. Inference module 232 controls the manner by which decision-support module 210 generates solutions to the known or unknown medical conditions of the patient. Stated another way, inference module 232 generates the decision-supported patient data based upon the newly gathered patient data, stored patient data within patient module 220, and the knowledge base contained within knowledge module 226. For example, inference module 232 may use the genetic susceptibilities of the patient to identify the various medical conditions that the patient may be susceptible to in the future and prescribe medical care recommendations to reduce the likelihood of such medical conditions occurring.

Inference module 232, in one embodiment, includes one or more inference engines 233 and an application module 235 to drive the one or more inference engines 233. The one or more inference engines 233 apply the rules and parameters stored in knowledge module 226 to generate the medical diagnosis and the medical care recommendation for the patient. Application module 235, in one embodiment, includes the software modules to cause inference engine 233 to generate such medical diagnosis and medical care recommendations. The functionality and operation of these elements are commonly known by one skilled in the art and need not be discussed further herein. A variety of other modules and components may be included within inference module 232 as known by one skilled in the art in light of the teaching contained herein.

As illustrated, inference module 232 is depicted as being incorporated within decision-support module 210. One skilled in the art may appreciate that inference module 232 may optionally be integrated with medical module 216 by connecting decision-support module 210 directly to medical module 216 by an Internet Inter-Object Request Broker Protocol (IIOP) or remotely by a Remote Method Invocation (RMI). Alternatively, inference module 232 may be incorporated partially or completely within medical module 216 and hence decision-support module 210 is devoid of inference module 232. Additionally, inference module 232 may be incorporated within an application server hosted by decision-support module 210 or may be incorporated within an application server hosted by medical module 216.

Decision-support module 210, in one embodiment, includes an optional progress note module 236. Progress note module 236 communicates with inference module 232 to receive the decision-supported patient data and subsequently generate a decision-supported progress note. The decision-supported progress note presents the clinician with the decision-supported patient data in a standardized and reproducible configuration so that system 200 minimizes the potential for misdiagnosis of a medical condition or recommended medical treatment based upon the illegibility of a clinician's notes. Furthermore, the decision-supported progress note provides a clinician with a standardized format for collecting additional patient data and a list of recommended follow-up questions, tests, and other medical care to perform during a physical exam or visit with the patient. Optionally, the clinician may modify the particular configuration of the progress note so that the clinician may more effectively give medical care to a patient. Consequently, progress note module 236 may allow a clinician to define how the decision-supported patient data is to be displayed in the decision-supported progress note.

In one setting, a clinician may request that progress note module 236 summarize the decision-supported patient data generated by inference module 232. The summarized decision-supported patient data contains the pertinent information related to the medical condition of the patient in an easily viewed display. For example, if the patient has diabetes, progress note module 236 will generate a decision-supported progress note that summarizes the pertinent medical parameters associated with the patient's diabetes, such as the most recently acquired heart rate, blood pressure, blood sugar level, and the like, while providing warnings or alerts to the clinician. Similarly, when a therapeutic regimen is suggested, progress note module 236 summarizes decision-supported patient data includes drug name and type, dose, route, interval and duration of therapy specific to the patient and the drug, patient demographics, and the like, while providing warnings or alerts to the clinician.

In this manner, progress note module 236 may provide the clinician with the pertinent patient specific decision-supported patient data in a summarized arrangement requested by the clinician. By summarizing the pertinent data, a clinician more capably treats a patient in an efficient manner.

In another configuration, progress note module 236 generates a decision-supported progress note that includes a calendar representing when a patient is to take medication that is prescribed by the clinician. Optionally, the calendar includes a visual representation of the medication prescribed. For example, if the clinician prescribes 1000 mg of ganciclovir then the calendar may include a visual representation of two (2) 500 mg pills containing ganciclovir. In this manner, the calendar both reminds the patient when to take their medication, while also giving a visual representation of the number of the pills prescribed.

To allow inference module 232 and/or progress note module 236 to transceive information to and from user module 214, decision-support module 210 optionally includes a web module 238. Web module 238, in one embodiment may be a web server that facilitates data transceiving between decision-support module 210 and user module 214. Web module 238, either alone or in combination with inference module 232 and/or progress note module 236 may control how and when the decision-supported patient data is presented to the clinician and/or patient. For example, in one embodiment, web module 238 provides the decision-supported patient data by way of a web page that is accessible by clinicians and/or patients via user module 214. Therefore, web module 238 defines the layout or format of the web page. Optionally, the clinician and/or the patient may vary the particular configuration of the web page upon which they will view the decision-supported patient data.

One skilled in the art may identify various other configurations of web module 238 that are applicable. For example, in one configuration, web module 238 automatically delivers patient data to the clinician as the clinician accesses web module 238, such as broadcasting updated patient data. In still another configuration, such as with an inpatient setting, web module 238 continually or periodically updates the decision-supported patient data or decision-supported progress noted and subsequently transmits (or broadcasts) warning or alerts to the clinician based upon the updated patient data. For instance, upon completing laboratory tests a laboratory clinician may broadcast the updated laboratory results to decision-support module 210 by way of laboratory module 262. Subsequently, web module 238 updates decision-support patient data and decision-supported progress notes and delivers a notification or warning to the clinician's user module, such as a pager, telephone, PDA, a clinician's assistant that may forward the notification or warning, some third party service provider or the like. In another configuration, web module 238 delivers patient data, decision-supported patient data, and/or decision supported progress note to third party module 218. For example, if decision-support module 210 identifies that as a medical care recommendation the patient may be referred to a specialist, upon authorization by the clinician, web module 238 delivers a decision-supported progress note to the clinician with a referral request to an identified clinician or to an insurance carrier or other medical provider. Subsequently, upon authorization from the clinician, web module 238 may send the referral request directly to an identified clinician or to an insurance carrier or other medical provider. In another configuration, web module 238 allows a patient or clinician to request additional information via electronic mail (e-mail) or by some other manner from a group of specialists. For example, a clinician may identify that a patient has contracted tuberculosis and request guidance from a medical care specialty group (such as third party 218) on what actions to take in light of the medical condition. In response, the specialty group or a clinician part thereof may response the to clinician's request via e-mail or some other manner, such as telephone, videoconference, and the like.

Web module 238 may transceive information and data via Hypertext Transfer Protocol (HTTP), File Transfer Protocol (FTP), Wireless Application Protocol (WAP), or various other communication protocols and communication line connections. One skilled in the art may identify various other communication protocols and connections that are applicable for allowing web module 238 to transceive data between user module 214 and medical module 216. For example, web module 238 may use TCP/IP communication protocol, a connection orientated or connectionless network protocol, via asynchronous transfer mode (ATM) technology, X.25 protocol, Frame Relay protocol, packet switching protocols, circuit switching protocols, dynamic packet switching protocols, 802.11RF protocol, and the like to transceive data through network 212. Therefore, web module 238 and hence decision-support module 210 may use a variety of different interface types, such as but not limited to a wireless interface thereby utilizing IR, RF, satellite, blue tooth transmission and associated protocols, a modem, cable modem, ADSL connection, ISDN, Ethernet, or similar other connections, and the like.

One skilled in the art may appreciate that inclusion of web module 238 within decision-support module 210 is optional. In the event that decision-support module 210 is partially or completely incorporated within medical module 216, decision-support module 210 is devoid of web module 238 and may utilize an appropriate web module incorporated within medical module 216 to allow communication with user module 214 via network 212.

Optionally included within decision-support module 210 is a billing module 240. Billing module 240 is configured to communicate with web module 238 and generate the appropriate billing codes and proper documentations required to allow accurate billing of medical care to insurance carriers, government agencies, Medicare, and the like. Once a clinician has completed a patient examination, web module 238 receives the clinician's authorization for the medical care proscribed. Subsequently, billing module 240 tracks the medical care authorized by the clinician for each patient and creates the billing codes and documentation for each procedure, drug prescribed, test requested, and the like. Although billing module 240 is depicted as being incorporated within decision-support module 210, one skilled in the art may recognize that billing module 240 may be take the form of a stand-alone module. Alternatively, billing module 240 may be incorporated within medical module 216. Optionally, billing module 240 may communicate with medical module 216 and generate the billing codes and documentation through the medical facilities accounting, administration, or other facilities.

Referring again to FIG. 3, communicating with decision-support module 212 is user module 214. User module 214 allows a clinician and/or patient to gather patient data and subsequently receive real-time or perceived real-time decision-supported patient data or decision-supported progress notes. User module 214, as mentioned above, may take the form of computer 20 and/or remote computer 49*a* and 49*b* that allows a clinician and/or patient to gather and view medical information and associated medical diagnoses and treatments. Illustratively, user module 214 may be a personal digital assistant (PDA) or other hand-held hardware device, including, but not limited to, a Palm Pilot, or CE based palm computer, with associated software applications and operating systems, a general purpose computer, a special purpose computer, a pager, a wireless telephone, pocket PC, and the like. Additionally, such user modules 214 may synchronize or communicate with decision-support module 212 to transceive patient data, decision-supported patient data, and decision-supported progress notes on a continuous, substantially continuous, periodic, and/or sporadic manner. Such synchronization or communication may be achieved through wireless, direct dial, desktop or some other synchronization and by one of a variety of communication line connections as discussed herein and known to one skilled in the art.

User module 214, in one embodiment, includes a communication interface 242, a control module 244, and a user interface 246. Communication interface 242 of user module 214 is adapted to transceive data between decision-support module 210, medical module 216, and user module 214. Depending on the type of communication line connection between modules 210, 214, and 216, communication interface 242 may have a variety of configurations and perform a number of functions. For example, communication interface 242 may be a wireless interface thereby utilizing IR, RF, satellite, blue tooth transmission and associated protocols, a modem, cable modem, ADSL connection, ISDN, Ethernet, or similar other connections and other communication line connections known to one skilled in the art in light of the teaching contained herein. Additionally, communication interface 242 may compress, decompress, encrypt, decrypt, and perform such other functions as known by one skilled in the art.

As implied above, communication interface 242 communicates with control module 244. Control module 244 performs a number of operations and functions to allow a clinician and/or patient to gather patient data through user interface 246. Additionally, control module 244 manages the flow of decision-supported patient data and decision-supported progress notes to user interface 246. Control module 244, therefore, optionally manages the flow of patient data: (i) to and from the clinician and patient; (ii) from data storage module 248 to user interface 246; (iii) between user module 214 and decision-support module 210; and (iv) from medical module 216 to user module 214.

In addition to controlling the flow of patient data between the various modules and components of system 200, control module 244 may control the configuration of user interface 246. Stated another way, control module 244, in one embodiment, may receive display instructions from the clinician regarding how the decision-supported patient data and decision-supported progress note received from decision-support module 210 is to be displayed or arranged. Control module 244 may deliver such instructions to web module 238 or progress note module 236 for such modules to prepare the decision-supported patient data in accordance with the clinician's instructions. Alternatively, control module 244 may either receive the decision-supported patient data (or the decision-supported progress note) and convert the data into a form consistent with the clinician's instructions or function with inference module 232, progress note module 236, and web module 238 to generate the desired display.

In the later case, control module 244 may: (i) receive through communication interface 242 the decision-supported patient data or the decision-supported progress note; (ii) store the decision-supported patient data or the decision-supported progress note in data storage module 248, decision-support module 210, medical module 216, and/or third-party module 218; (iii) summarize the decision-supported patient data (or decision-supported progress note) in accordance with the clinician's instructions to display the pertinent information to the clinician; and (iv) display the summarized decision-supported patient data (or decision-supported progress note) to the clinician through user interface 246.

Optionally, control module 244 may vary the display configuration requested based upon the particular hardware device and software modules that will present the decision-supported patient data or decision-supported progress note. For example, the limitations on allowable display configurations is greater for a PDA or "thin" client than for a general purpose computer; hence control module 244 may limit or eliminate the allowable choices or merely display the decision-supported patient data in a form applicable for the particular hardware device no matter the clinician's instructions.

In addition to controlling the manner by which the decision-supported patient data is to be displayed to the clinician, control module 244 may allow the clinician and/or patient to access detailed patient data or decision-supported patient data stored in decision-support module 210 or medical module 216. Alternatively, control module 244 may display the decision-supported patient data, without summarizing the information associated with the decision-supported patient data.

Control module 244 may include various hardware and/or software modules to perform the above-referenced functions, such as but not limited to one or more microcontrollers, central processing units, state machines, programmable logic arrays, network logical arrays, or gates, ASIC processors, software-based controllers, combination logic, combinations thereof, and a variety of other controllers known by one skilled in the art. Control module 244 may communicate with communication interface 242, user interface 246, and data storage module 248 by a variety of connections, such as but not limited to electrical communication, an analog or digital, wireless, optical, or various other types of connection by way of one of a variety of communication line connections known by one skilled in the art.

As referenced above, a clinician or patient may update the patient data, the decision-supported patient data, and the decision-supported progress note through user interface 246. Similarly, the clinician or patient may receive a graphical representation of all or a summarized version of the available the patient data, the decision-supported patient data, and the decision-supported progress note through the same user interface 246. Optionally, a clinician may control the amount of patient data, whether decision-supported or not that the patient may view through user interface 246.

User interface 246, either alone or in combination with control module 244 and decision-support module 210, may allow a clinician or patient to define the display format of the decision-supported patient data and other patient data transmitted to user module 214 from decision-support module 210 and/or medical module 216. A clinician may, in one embodiment, select from a number of stored display configurations, use the default display configuration, or generate a clinician specific display configuration. No matter the particular display configuration selected by the clinician, the particular display configuration assists a clinician in diagnosing, treating, and providing medical care to the patient.

In one embodiment, user interface 246 is a web browser. One skilled in the art may identify various other interfaces that are capable of performing the desired function of allowing a clinician and/or patient to gather and subsequently view medical information. For example, user interface 246 may be a graphical user interface (GUI), textual, interactive, drop-down menu, voice activated, and the like interface. User interface 246 may allow a user to select choices through pushing buttons, selecting icons, scanning bar codes, vocalization of procedure codes or medical treatments, or through some other method, system, hardware device, and/or software application known to one skilled in the art. The above described interfaces may be developed from a variety of software packages such as HTML, dynamic HTML (DHTML) (including JavaScript, Cascading Style Sheets, Common Gateway Interface (CGI) scripts, cookies, Java, ActiveX, Server-Side Includes (SSI)), and the like.

According to another aspect of the present invention, system 200 includes medical module 216. As depicted in FIG. 3, medical module 216 optionally includes a web module 252 that communicates with network 212. Web module 252, such as a web server, delivers the information stored in medical module 216 over network 212 to those hardware and/or software modules that access web module 252 and have appropriate access rights. Upon receiving a request from a hardware and/or software module, such as user module 214 or decision-support module 210, web module 252 provides the requested documents or information in an appropriate language, such as Hyper Text Markup Language (HTML), XML, or some other language. Web module 252 may provide the requested information via Secured Socket Layers (SSL) protocol, a Virtual Private Network (VPN), asymmetric or symmetric encryption, or some other security protocol or process known to one skilled in the art. One skilled in the art may also recognize that although a single server is depicted as part of medical module 216, medical module 216 may include a plurality of web modules 252.

Communicating with web module 252 is an application module 254, such as an application server. Application module 254 provides the conduit between the information stored in medical module 216 and any requests for such information through web module 252. Application module 254 acts as an intermediary between the information or data storage of medical module 216 and the hardware and/or software modules that request access to the desired information. In the illustrated configuration of FIG. 3, such information from the ancillary module 256 may pass through application module 254 upon a request through web module 252 to access the medical information stored in the ancillary module 256. Alternatively, such information may be directly delivered to decision-support module 210 over a secure connection.

According to another aspect of the present invention, medical module 216 includes ancillary module 256. Ancillary module 256 includes one or more other modules that represent the various hardware and/or software modules of the individual departments within the medical facility, such as the hospital or clinic, and their associated connection to medical module 216 and network 212. As illustrated, ancillary module 256 may include a pharmacy module 260, laboratory module 262, admit/discharge/transfer module 264, radiology 266, and the like. One skilled in the art may identify various other modules that may be included within ancillary module 256. For example, ancillary module 256 may include computer physician order entry systems, other order entry systems, and the like.

Generally, pharmacy module 260 maintains information and data representative of drugs requested and proscribed for each of a plurality of patients, whether a patient is an inpatient or an outpatient. Similarly, laboratory module 262 maintains information and data representative of the laboratory tests ordered and performed for each of a plurality of patients. Admit/discharge/transfer module 264, in this configuration, maintains information and data representative of the billing information and scheduling information associated with each of a plurality of patients, while radiology module 266 maintains information and data representative of the Computed Tomographic (CT) scans, fetal ultrasounds, magnetic resonance imaging (MRI), mammographs, and X-rays, ordered and performed for each of a plurality of patients.

Generally, system 200 suggests the various embodiments or configurations by which the present invention may be implemented for various network configurations. For example, when network 212 is the Internet, system 200 illustrates the communication of clinicians and patients with a decision-support module 210 having the configuration of a web site. In this manner, decision-support module 210 acts as an application service provider where the modules and components of decision-support module 210 are centrally located and connected to via a secure Internet connection. To access decision-support module 210 a clinician and/or patient pays a regular subscription fee and uses a traditional web browser, such as Microsoft® Internet Explorer, Netscape, and the like. This particular configuration reduces the installation costs for those medical facilities that wish to utilize the beneficial properties of the present invention. However, this configuration requires the clinician and/or patient to input the patient information to be stored in patient module 220.

Alternatively, when network 212 is a LAN, system 200 illustrates the communication of clinicians and patients with decision-support module 210 that is integrated with medical module 216, as illustrated by the dotted lines in FIG. 2. Such integration may be achieved by connecting inference module 232 of decision-support module 210 directly to application module 254 of medical module 216 by an Internet Inter-Object Request Broker Protocol (IIOP) or remotely by a Remote Method Invocation (RMI). In this configuration, clinicians and patients obtain the decision-supported patient data (or the decision-supported progress note) via a secure intranet using one of a variety of web browsers known to one skilled in the art. In this manner, decision-support module 210 may be integrated with medical module 216 and may receive patient data stored in patient module 220 and/or ancillary module 256. The medical module 216 and the individual modules included within ancillary module 256 may be considered as an electronic medical record (EMR) system that is typically used within the medical field.

In still another configuration, again when network 212 is a LAN, system 200 illustrates the communication of clinicians and patients with decision-support module 210 that is integrated with application server 254 of medical module 216. In this configuration, ancillary module 254 acts as patient module 220 and requests decision-supported patient data (or decision-supported progress notes) from inference module 232 and progress note module 236 directly. This is achieved by interfacing application server 254 with knowledge module 226, whether or not knowledge module 226 resides on application server 254. In this configuration, a clinician receives decision-supported patient data transparently without the clinician switching to a different application or having to learn new software products.

Figure 4:
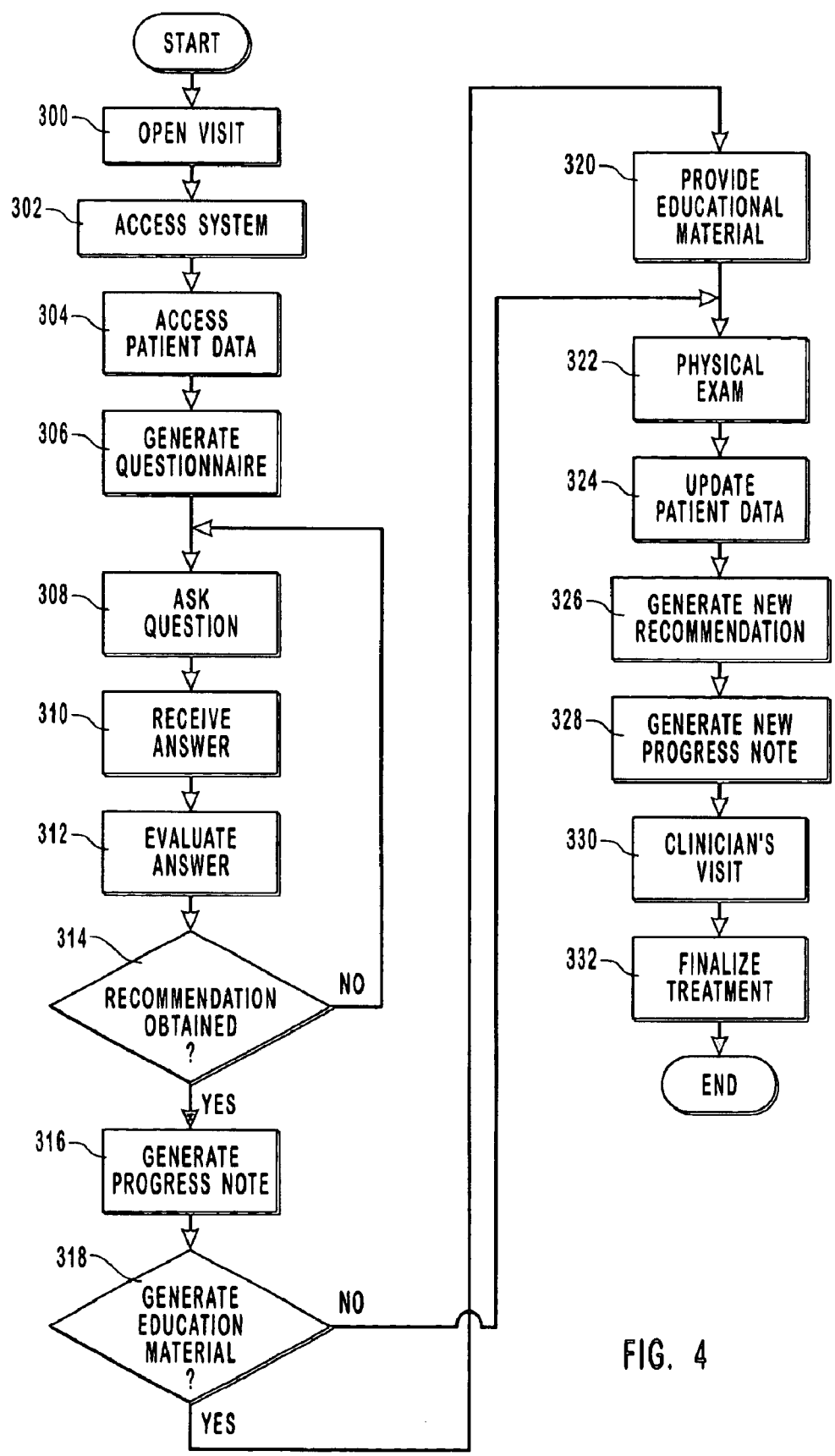
FIG. 4 is a flow diagram representing data flow through the system of FIGS. 2 and 3 in an outpatient setting.
Figure 5:
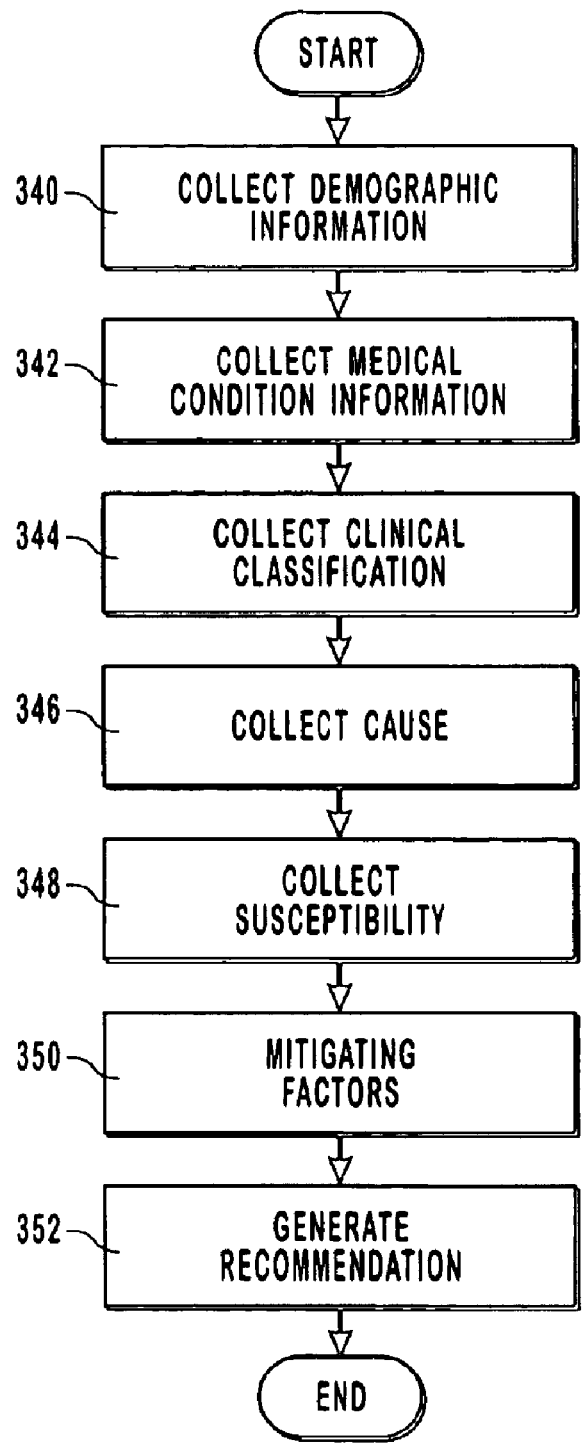
FIG. 5 is a flow diagram representing data flow through the system of FIGS. 2 and 3 in an outpatient setting where an unknown medical condition is identified.

FIGS. 4 and 5 are flow diagrams representing the operational process of providing medical care by a clinician in an "outpatient" setting, such as at a clinic. The discussions will be generalized with respect to the configuration of system 200 with respect to the interaction of decision-support module 210, user module 214, and medical module 216 through network 212, i.e., whether network 212 is a LAN, WAN, the Internet, and the like. It may be appreciated, that the method steps described herein are only illustrative of one method of performing the desired function.

Referring now to FIG. 4, a description of the methodology of the present invention shall be provided as it relates to obtaining decision-supported data by a clinician in an outpatient setting, where the patient has known medical conditions, such as diabetes. The methodology description refers to FIGS. 2 and 3, thereby illustrating the method of processing data through the various illustrative modules and components of the present invention.

Initially, in an "outpatient" setting, such as in a clinic, a patient arrives at the clinic and is admitted, or otherwise identifies themselves as having an appointment to meet with the clinician, as represented by block 300. Upon paying any fees and completing any admission paper work, the patient may access a user module 214 by providing the patient's name, birth date, social security number, or the like. By giving the identification information, the patient gains access to system 200, as represented by block 302. For example, in one embodiment a patient provides the identification information through a cathode ray tube (CRT) monitor with a touch sensitive user interface 246.

Upon accessing system 200, decision-support module 210 accesses patient specific information contained within patient module 220, as represented by block 304. Based upon the patient's identification information, decision-supported patient data from decision-support module 210 is used to generate standardized questions to be asked of the patient, as represented by block 306. Alternatively, control module 244 may receive the standardized questions from data storage module 248 of user module 214. In either case, the standardized questions may be modified by any of the patient's pre-existing medical conditions. For example, in this illustrative example, the patient has diabetes and the questions asked by system 200 may be modified by one or more rules to thereby review the current medical condition of the patient with respect to their diabetes.

As the patient is asked questions, as represented by block 308, and provides answers, as represented by block 310, control module 244 tracks the answers and transmits the same to decision-support module 210. Upon receiving the answers, inference module 232 and/or knowledge module 226 (with associated rules) evaluate the responses, as represented by block 312, to determine whether additional information is need to generate a recommendation. Until a recommendation is reached, system 200 will continue to ask questions, receive answers and evaluate answers, as represented by decision block 314.

Once a recommendation is reached, if a recommendation is required, system 200 generates a decision-supported progress note that may be used by the clinician during a physical examination of the patient, as represented by block 316. For example, the decision-supported progress note can provide the clinician with a ranked list of recommendations with side-effects or problems associated with each recommendation.

In the event that the question and answer session results in decision-support module 210 identifying educational materials that may aid the patient with their medical condition, user module 214 may prompt the patient as to the desirability of obtaining such educational materials, as represented by decision block 318. If the patient wishes the educational materials, user module 214 may retrieve such information from data storage 248 or alternatively from decision-support module 210 and/or medical module 216 and print or otherwise deliver the materials to the patient, as represented by block 320. Optionally, system 200 may always provide the patient with the educational material, without the patient having the option to select whether they receive the educational materials.

Following receipt of the educational materials, whether receipt occurs before or after the decision-supported progress not is created, the patient receives a brief physical exam, such as height, weight, blood pressure, and the like by a clinician's assistant, or optionally the clinician, as represented by block 322. The newly obtained physical exam data is input into system 200 through user interface 246 and the patient data is updated, as represented by block 324.

Upon receiving the updated patient data, inference module 232 reevaluates the recommendation previously developed in light of the updated patient data, as represented by block 326. This new recommendation, as with the previous recommendation may be based upon not only the medical information contained in knowledge module 226 but may be based upon the patient's insurance provider, the cost of the drug or other treatment, effectiveness of the treatment, and such other factors as known by one skilled in the art.

Subsequently, decision-support module 210 applies the same or different rules to generate a new decision-supported progress note, as represented by block 328, which is delivered to the clinician so that the clinician may complete the clinician's examination of the patient, as represented by block 330.

To complete the "outpatient" process, the clinician may review the questions or other information that decision-support module 210 has identified as a medical area requiring a more detailed analysis of the patient's medical condition. For example, although a patient may be visiting the clinician for a scheduled check-up, the patient's responses to the posed questions may suggest another medical conditions, such as an unknown disease, or other medical condition.

Referring now to FIG. 5, an illustrative process for identifying and recommending a treatment for an unknown disease is depicted. Continuing with the above-described illustrative example, a patient with a known disease, such as diabetes, is determined to have an unknown disease. Initially, the clinician may review the patient's medical history contained within decision-support module 210 or optionally collect new patient history or demographic information, as represented by block 340

Following receipt of the demographic information, the clinician may collect disease information, as represented by block 342. This may be obtained through laboratory tests or from the question and answers provided to the clinician by system 200. Furthermore, the question and answers used to initially collect current medical information may be used to collect medical condition information regarding the patient's relatives. Therefore, system 200 may analyze the patient's predisposition for particular medical conditions in light of the newly gathered or stored patient data.

Let us assume that the unknown medical condition is a disease. Once the disease is identified, a clinical classification is identified based upon the disease, as represented by block 344. For example, let us assume that the disease is identified as pneumonia; the clinical classification may include deciding whether the pneumonia is to be treated with outpatient therapy or inpatient therapy. Alternatively, the clinician may select an undecided choice, thereby allowing system 200 to give the clinician information regarding the possible benefits of one or other of the possible therapy regimes. When the clinician is undecided or uncertain as to whether the patient should be treated as an inpatient or an outpatient, the clinician may optionally access or be prompted to access information within knowledge module 226 that gives the clinician the criteria for admission.

Following the therapy clinician classification, the acquisition clinician classification may be determined. The clinician may determine whether the medical condition was hospital acquired (HAP) (ventilator associated or non-ventilator associated), nursing home acquired, HIV-associated pneumonia, Cystic Fibrosis-associated pneumonia, or community acquired (CAP).

Once the clinical classification is identified, the rules control the manner by which system 200 collects the etiology based on the clinical class, as represented by block 346. This may include distinguishing between an uncertain organism requiring an empiric therapy and an organism identified through laboratory results. For example, the organism may be a gram-positive (GP) bacteria, such as *Streptococcus pneumoniae* (*S. pneumoniae*) or *Staphylococcus aureus* (*S. aureus*) or a gram-negative (GN) bacteria, such as *Hemophilus influenzae* (*H. influenzae*), *Klebsiella pneumoniae* (*K. pneumoniae*), *Moraxella catarrhalis, Pseudomonas aeruginosa* (*P. aeruginosa*), or *L. pneumophila*. If the organism is an atypical pathogen the clinician may select from a list of appropriate pathogens depending upon the type of acquired pneumonia. For example: (i) an Atypical bacterial, such as *M. pneumoniae* or *Chlamydia pneumoniae*; (ii) Rickettsiae, such as *Coxiella burnetii* (Q Fever); (iii) an Acid-fat bacteria, such as *M. tuberculosis* or MAC complex; (iv) a Fungi/Protozoa, such as *Coccidiodomycosis, Histoplasmosis, Blastomycosis, P. carinii*; (v) a virus, such as Influenza A, Influenza B, Hantavirus, and the like. For example, if the pneumonia is community acquired (CAP) the clinician may be given the options of *Legionella, Mycoplasma, Influenza, Chlamydia pneumoniae, Chlamydia psittaci, Coxiella burnetii* (Q Fever), and the like. Similarly, if the organism is a Pyogenic pathogen and community acquired, the clinician may select from *Streptococcus pneumoniae, Hemophilus influenzae, Staphylococcus aureus*, Group A *Streptococcus, Pseudomonas aeruginosa, Klebsiella pneumoniae, Neisseria meningitides, Moraxella catarrhalis*, and the like.

Following receipt of the etiology, the rules may present the clinician with various genetic or other susceptibilities of the disease if etiology is organism specific, as represented by block 348. In this manner, the clinician may define the etiology of the organism. In this particular example, let us assume that the organism is identified as *Staphylococcus aureus*. The clinician may provide system 200 with information related to the organism's susceptibilities within the particular patient. For example, the organism may be resistant to linezolid, oxacillin, vancomycin, and dalfopristin-quinupristin. Alternatively, the clinician may not know the susceptibilities thereby relying on system 200 to recommend a treatment that may work.

Upon defining any organism susceptibilities, the rules used by inference module 230 may aid the clinician in defining one or more mitigating factors based upon the etiology, as represented by block 350. The clinician may define factors that may have caused the pneumonia. For example, the patient may have recently aspirated, be immunosuppressed, recently received antibiotics, and the like. Additionally, the mitigating factors may be specific to whether the organism is identified or whether the empiric therapy is to be used for an unknown organism. For example, for an identified organism the clinician may provide information related to abnormal kidney function, Anti-microbial resistance, current or recent treatment failure, and the like. Similarly, if the organism is unknown, the clinician may define information and data related to Abnormal kidney function, Recurrence/relapse, Age, Comorbidities, Severity/Acuteness of illness, Neutropenia, Neutropenia with IV access, Neutropenia and fever despite therapy, Aspiration, Suspicion of organism (esp. HAP, CF), CD4 count (HIV), Disease stage (CF), and the like.

Following the data collection, system 200, and more specifically, decision-support module 210 generates a recommendation for treatment of the patient, optionally using the information gathered by the clinician, the stored patient data, mircorbial susceptibilities and genetic predispositions based upon the patient's family history and relative's medical conditions, the rules, as represented by block 352. Such recommendation may entail decision-support module 210 analyzing: (i) patient's drug allergies; (ii) patient's genetic variations with regard to drug metabolizing enzymes or genetic predisposition to diseases; (iii) genetic variations in the patient's ability to metabolize specific drugs; (iv) drug-drug interactions; (v) dosing requirements based on height, weight, age, sex, and the like; (vi) price; (vii) probability of success for curing the disease; (viii) monographs; (ix) antibiograms or antimicrobial-susceptibility patterns; and (x) formulae of the drug.

System 200 may also use pharmacogenomic data to select particular medical treatment modalilties; thereby using a patient's genetic structure to define responses to prescribed drugs. For example, a patient may be found through genetic testing to lack an enzyme necessary for a particular drug's metabolism. Hence, decision support module 210 would use such pharamacogenomic information to suggest an alternative drug that avoids toxicity and treatment failure, while being consistent with the patient's condition and pertinent medical parameters.

Additionally, recommendations may include analyzing the need for a referral, other tests, microbial susceptibility or genetic predispositions to the disease or medical condition, family history, behavioral and lifestyle changes, and patient education related to the medical condition or avoiding the medical condition. In this manner, system 200 may optionally evaluate the patient's long-term risk for contracting or their predisposition or susceptibility to various medical conditions. Thus, decision-supported patient data or a decision supported progress note is created.

As mentioned throughout, the above-recited process to generate the decision-supported patient data and the decision-supported progress note may use one or more, rules and provide statements to the clinician to assist the clinician with making an informed decision of medical treatment. Such statements and rules, stored in knowledge module 226, are used by inference module 232 to make the decision-supported recommendation for treatment of the medical condition.

Illustrative rules and statements for the diagnosis and treatment of Pneumonia are represented in Tables 1–5 of FIGS. 6–10. As illustrated, Table 1 contains a plurality of rules that may be used by inference module 230 to generate the decision-supported patient data and the decision-supported progress note, thereby providing the clinician with a recommended medical treatment for a medical condition. Tables 2–5 (FIGS. 7–10) contain a number of rules specific to certain information collected by system 200; specifically, optionally sequentially activated rules associated with the analysis of mitigating factors, susceptibilities, and duration of treatment. One skilled in the art may appreciate that various other rules may be appropriate to generate a recommendation for treatment of Pneumonia.

The clinician determines whether the recommendation is correct by analyzing this recommendation. If correct, the treatment is finalized, as represented by block 332 of FIG. 4. Otherwise, system 200 and clinician progress through an iterative process to generate new recommendations based upon other factors that the clinician identifies using the same and/or additional rule specific to other medical conditions identified by the clinician.

It may be appreciated that one skilled in the art may perform the method described herein in a variety of manners, such as in differing order of steps, elimination of one or more steps, inclusion of all, some or addition steps, and the like. For example, steps 340–350 need not be performed by the clinician but are alternately performed by system 200 based upon patient data stored within patient module 220 and knowledge module 226. Additionally, the method may include various steps associated with system 200 prompting the clinician to complete a medchart to be sent to the Centers for Disease Control (CDC). Additionally, the above method may require checking with the CDC to determine whether a particular medical condition is gaining prevalence within a given regional area or to provide information to the CDC regarding the prevalence of the medical condition within the area that is served by the medical provider utilizing the beneficial properties of the present invention.

Figure 11:
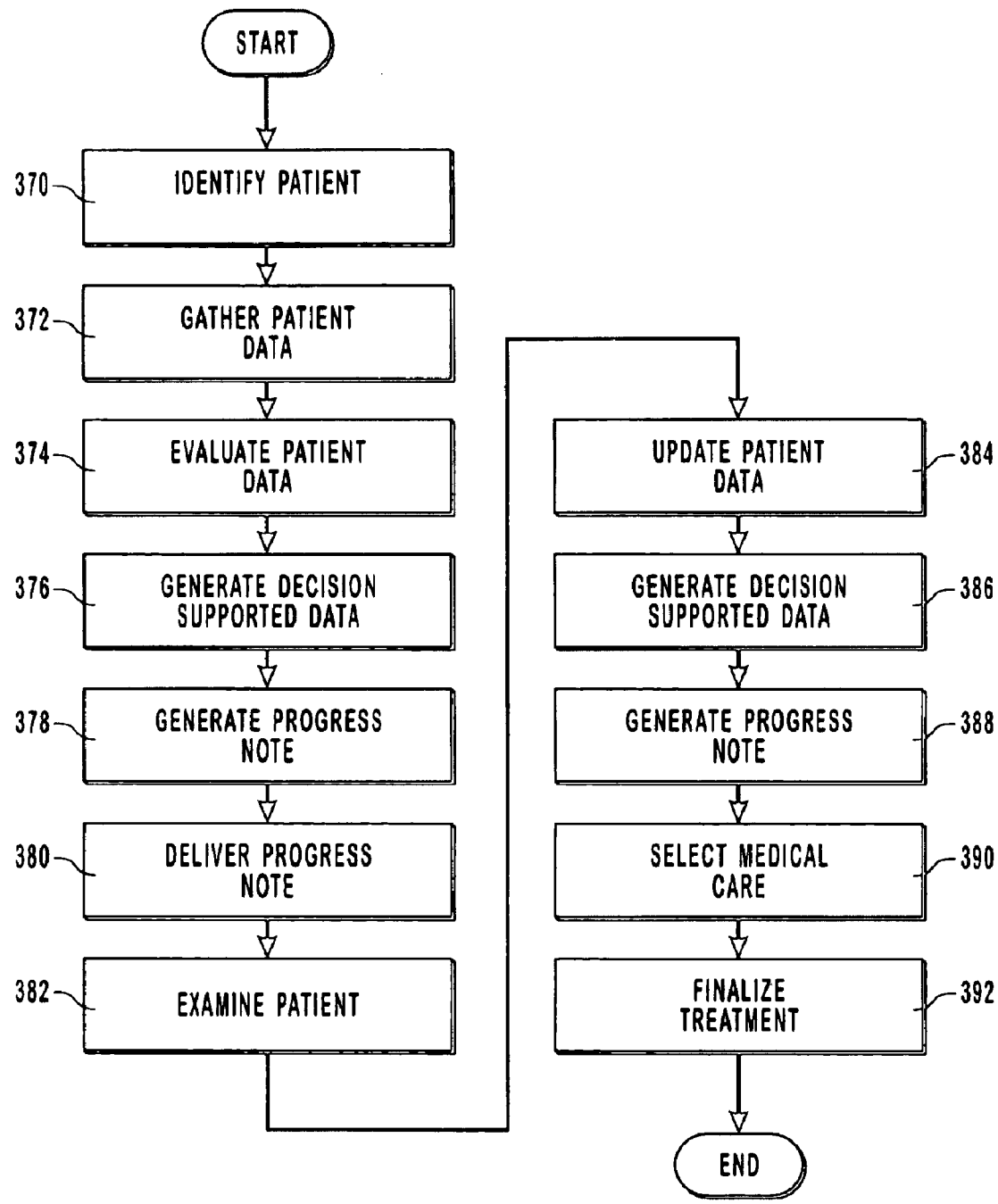
FIG. 11 is a flow diagram representing data flow through the system of FIGS. 2 and 3 in an inpatient setting.

Referring now to FIG. 11, an illustrative flow diagram for the treating a patient in an "inpatient" setting is depicted. Let us assume that the patient has a known medical condition, such as a urinary tract infection. During a visit with the patient, such as during "rounds", a clinician accesses system 200 through user module 214. Upon identifying the patient with whom he or she is visiting, as depicted by block 370, user module 214 requests the most up to date decision-supported patient data or decision-supported progress notes for the patient. Subsequently, decision-support module 210, either solely or in combination with medical module 216 gathers patient data for the patient selected, as represented by block 372. This may entail each or a combination of the following: (i) searching patient module 220, with its associated databases 222a–222n (FIG. 3); (ii) searching one or more modules of ancillary module 256 (FIG. 3) of medical module 216; and (iii) receiving patient data from the clinician through user module 214.

Once decision-support module 210 gathers the patient data, inference module 232 of decision-support module 210 updates the decision-supported patient data based upon the most current patient data with the data (such as one or more rules) stored within knowledge module 226, as represented by block 374. Decision-support module 210 then updates the decision-supported progress note for delivery to the clinician. Analysis of the patient data to update the progress note may be performed in a similar manner as that described with respect to FIG. 5.

For example, decision-support module 210 reviews the clinical classification of the infection defined by the clinician and system 200. In this example, decision-support module 210 retrieves information related to the urine collection method, i.e., clean catch, Foley catheter, no urine collected, or other method, verifies the interpretation of the patient's symptoms and signs made by the clinician, i.e., whether the infection is lower tract, upper tract, or asymptomatic, and confirms whether the patient is being treated as an inpatient or an outpatient. In this example, let us assume that the patient is an inpatient and has a lower tract infection.

Upon retrieving the clinical classification, decision-support module 210 retrieves the etiology of the organism. This may include an identified or unidentified organism. If the organism is unidentified, decision-support module 210 checks to see if any cultures are pending. This may require decision-support module 210 to communicate with ancillary module 256 of medical module 216, and more specifically laboratory module 262, to determine whether any cultures are pending. Otherwise, decision-support module 210 analyzes the previous decision-supported patient data and decision-supported progress note for data representative of a request for organism cultures.

If the organism is identified, decision-support module 210 retrieves the information regarding the organism's etiology. For example, as illustrated in FIG. 12, the infection may be a bacteria, fungi, a parasite, or a virus. If a bacteria, the organism may be categorized as having gram-negative rods (GNR), gram-negative cocci (GNC), gram positive cocci (GPC), gram-positive rods (GPR), or acid-fast bacteria. In one embodiment of the present invention, as illustrated in FIG. 12, decision-support module 210 defines the bacteria to a more specific degree, but for illustrative purposes, the categorization of the bacteria is sufficient to present one skilled in the art with the required information and explanation of the present invention. If the organism is a fungus, the fungus may be *Candida* spp. or Non-*candida* spp. Similarly, the particular parasite or virus may be defined. For this illustrative example, let us assume that the patient has *Chlamydia*.

Following obtaining the etiology, decision-support module 210 gathers any susceptibilities and any mitigating factors. In this particular example, no susceptibilities are necessary. In contrast, however, a number of mitigating factors may be displayed or presented to the clinician. Such mitigating factors may include, but are not limited to pregnancy or post-partum state, renal transplant or other immunosuppression, use of diaphragm prior to onset, recurrence, early relapse of initial treatment failure, diabetes, neurogenic bladder, recent urologic surgery/ instrumentation, obstruction or abnormal urological anatomy, duration of symptoms for longer than seven (7) days, age less than three (3) years, and the like. Each mitigating factor may include a rule stored in knowledge module 226 that may be used to guide the decision-support process of the present invention.

Upon completing the above analysis, decision-support module 210 generates an updated decision-supported patient data and decision-supported progress note with a ranked list of recommendations, as represented by blocks 376 and 378. In this example, decision-support module 210 also identifies whether the existing medical care is successful in treating the urinary tract infection and generates a recommendation based upon the current success of the regime.

The above-recited process to generate the decision-supported patient data and the decision-supported progress note may use one or more rules and present the clinician with one or more statements regarding the rule used, as illustrated in FIGS. 13–19. Such statements and rules, stored in knowledge module 226, are used by inference module 232 to make the decision-supported recommendation for treatment of the medical condition.

As illustrated, Table 6 contains a plurality of rules that are directed to the general decision-supporting process of determining a recommended medical treatment for a medical condition. The illustrated rules contain illustrative logic used to determine and display a particular medical treatment. When the recommended medical treatment is displayed to the clinician, the clinician may optionally select to obtain other medical treatments that would be equivalent to the medical treatment given to the clinician. For example, some of the illustrative rules contain recommended treatments that are underlined. Such medical treatments have associated equivalent medical treatments that the clinician may optionally review and select. For example, the recommended medical treatment may be the prescription of a certain classification of drug, such as fluoroquinolone. A clinician may operate user interface 246 to obtain the various equivalent medications within the class of fluoroquinolone.

Tables 7–11 (FIGS. 13–18) contain a number of rules specific to certain information collected by system 200; specifically, optionally sequentially activated rules associated with the mitigating factors, susceptibilities, and duration of treatment. The statements and rules contained in FIGS. 13–18 are specific to the diagnosis and treatment of Urinary Tract Infection; however one skilled in the art may appreciate that various other rules may be appropriate. Table 12 (FIG. 19) depicts illustrative medications that may be prescribed or recommended by decision-support module 210 with associated contraindications. Therefore, decision-support module 210 analyzes the patient's medical history to verify that the patient is not allergic or resistant to a particular recommended medication. If the patient is allergic or resistant, decision-support module 210 defines a new recommendation for the clinician.

As mentioned above, the decision-support progress note, generally, includes all pertinent patient data that relate to the recommended treatments suggested by decision-support module 210. For example, when a therapeutic regimen is suggested, such as when treating the urinary tract infection, the decision-supported patient data includes drug name and type, dose, route, interval, daily cost, duration of therapy, critical alerts and warnings specific to the patient and the drug, patient demographics, logic sectors (rules) that are specific to the patient and the medical condition or syndrome being treated that led to the suggested treatment, and the like. Such information will be specific to each patient. For example, the dose of the therapeutic drug may be defined by decision-support module 210 based upon the height, weight, age, gender, and past medical history of the patient, current laboratory test values, the patients pharamacogenomic data, and the like. Although the analysis performed by decision-support module 210 may not be illustrated or displayed to the clinician, such information may be provided to the clinician via user module 214 if requested by the clinician.

Once a decision-supported progress note is generated for the patient, decision-support module 210 delivers the decision-supported progress notes to the user module 214 through which the clinician has accessed system 200, as represented by block 380.

Upon receiving the required patient data (e.g., decision-supported patient data, patient data, and other patient specific information), the clinician may perform his or her examination of the patient, as represented by block 382. The examination may be a physical examination, a question and answer session, or a combination thereof. Following the examination, the clinician may update the information stored within user module 214, as represented by block 384.

Subsequently, user module 214 connects to decision-support module 210 to generate new decision-supported patient data and a progress note, as represented by blocks 386 and 388. Following receipt of the new decision-supported patient data, the clinician selects the desired medical treatment or regime, as represented by block 390.

Alternatively, instead of the clinician asking a number of questions as prompted by the clinician's knowledge and information contained within the decision-supported patient data, a patient may answer a number of questions posed through another user module located at the patient's bed. In this manner, when the clinician examines the patient the clinician merely has to select the desired medical treatment or regime, without connecting to decision-support module 210 to obtain new decision-supported patient data. Hence, steps related to connecting to decision-support module 210 to obtain new decision-supported patient data are optional to the flow diagram depicted in FIG. 11.

Once the desired medical treatment or regime is selected, the clinician updates decision-support module 210, and optionally communicates with the necessary sub-modules of ancillary module 256 to request the desired treatment, as represented by block 392. For example, in the event that the medical care recommended by the clinician requires laboratory tests, user module 214 connects to laboratory module 262 to schedule such tests and notifies the nurse or other clinician assistant to obtain the necessary blood or other substances to perform the desired tests. Similarly, if a prescription medication is required, user module 214 connects with pharmacy module 260 to obtain the medication.

EXAMPLE

Following hereinafter is a generalized discussion of the manner by which decision-support system 200 may be used to provide the clinician with decision-supported patient data and one or more decision-supported progress notes where the medical condition is Meningitis. The example provides more specific rules and parameters related to Meningitis, while further illustrating the flow of data through system 200.

Figure 20A:
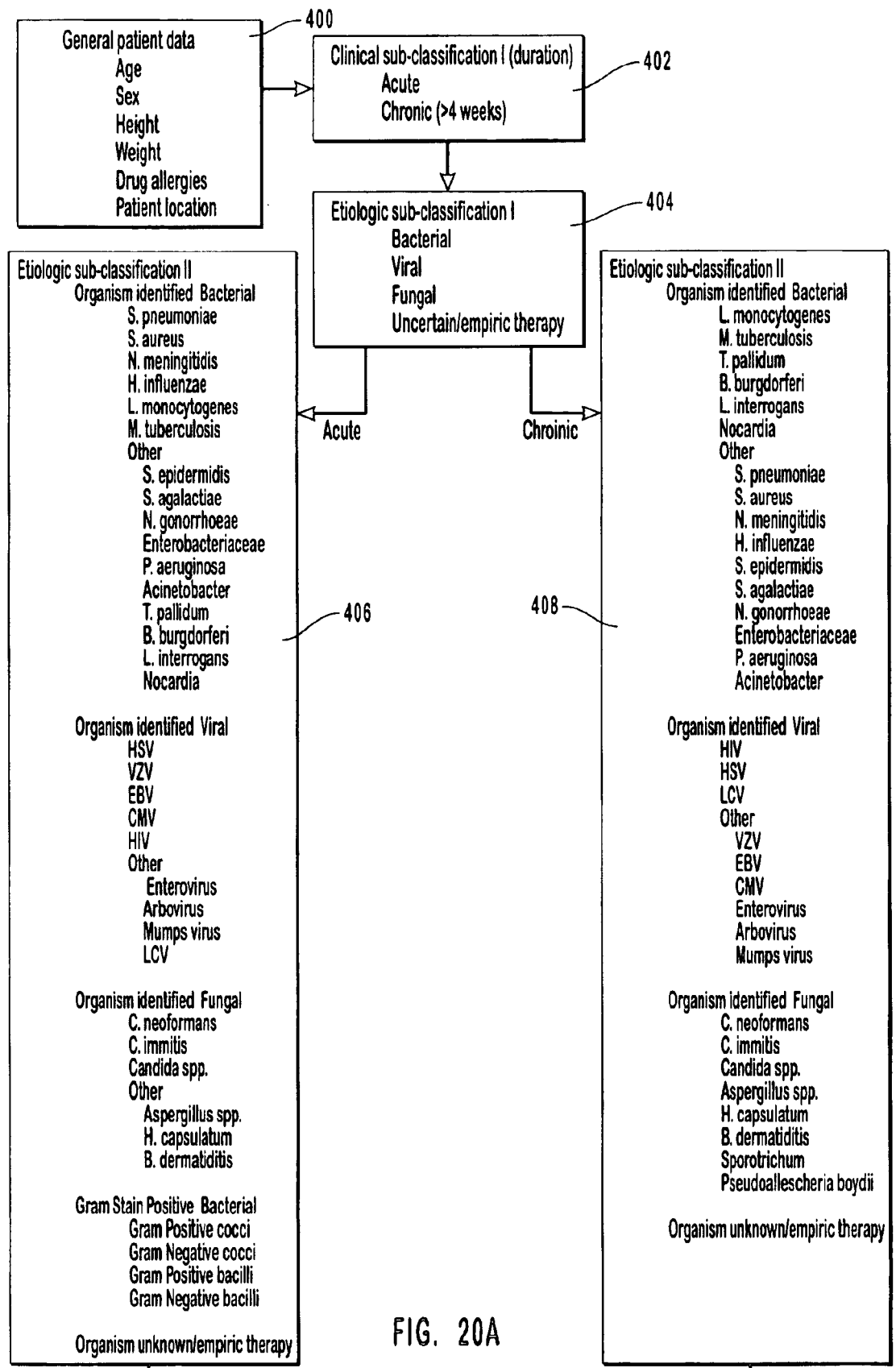
FIG. 20A–B is a schematic representation of the decision-support process for a medical condition of meningitis.
Figure 20B:
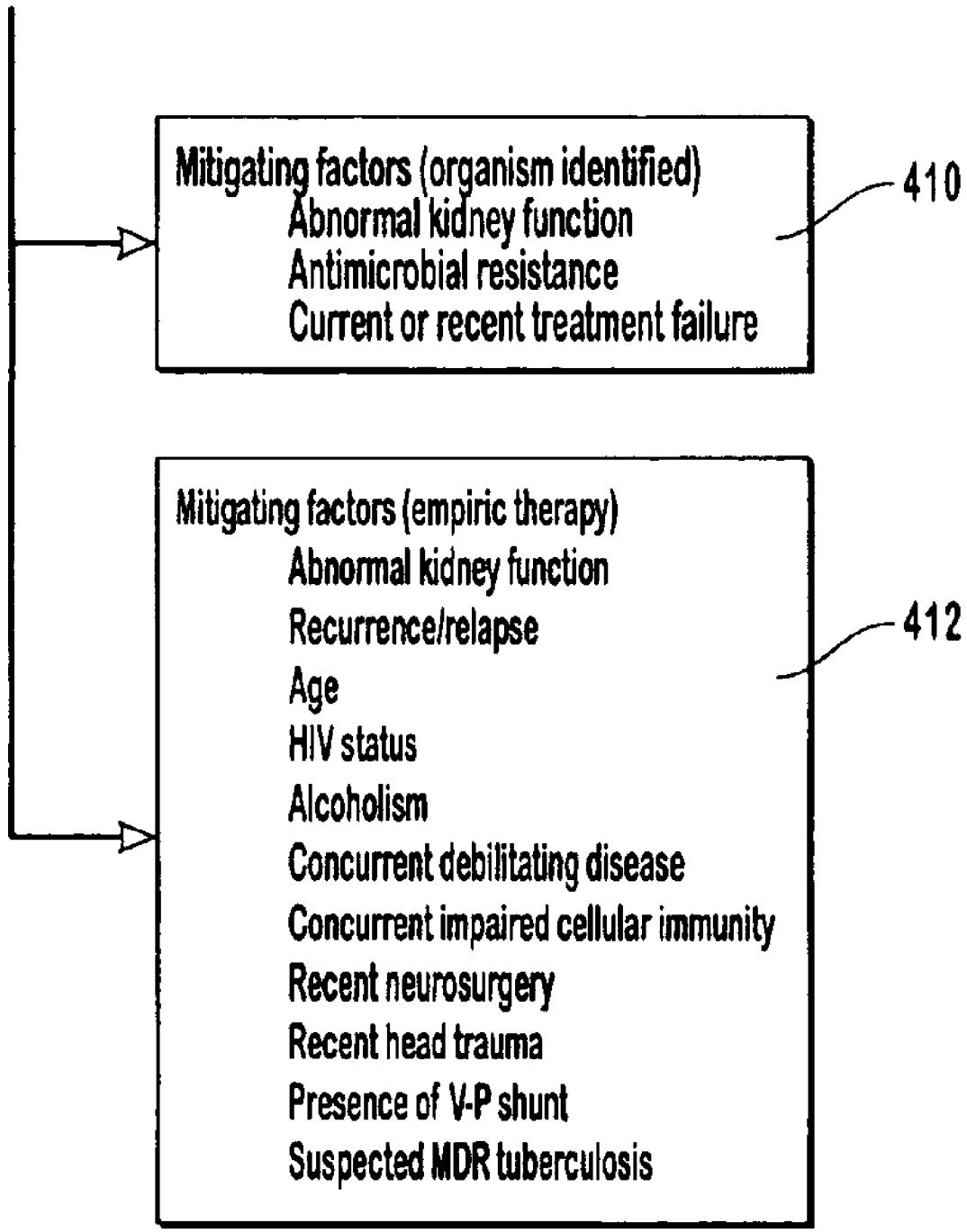

Referring now to FIGS. 20A–B, a schematic representation of the decision-support process described herein is depicted. As shown, general patient data is obtain by reviewing the medical history or demographic information, as represented by block 400

Following receipt of the demographic information, the clinician may collect disease information such as discussed above. For example, the disease information may be obtained through laboratory tests, from the question and answers provided to the clinician, patient data previously collected, based upon susceptibilities and genetic information associated with the patient's relatives, and the like. Once the disease is identified, a clinical classification is identified based upon the medical condition, as represented by block 402. We are currently assuming that the medical condition meningitis. The clinical classification of meningitis may include determining the duration of the meningitis to thereby decide whether the meningitis is acute or chronic. Different decision-support processes are taken depending if the meningitis is acute or chronic as may be discussed hereinafter.

Once the clinical classification is identified, system 200 collects the etiology based on the clinical classification, as represented by block 404. This may include distinguishing between a bacterial, viral, fungal, and an uncertain etiological classification. Subsequently, the etiology of the disease is determined based upon whether the meningitis is acute or chronic. If acute, the infection may be selected from those listed in block 406 or remain unidentified. Alternatively, system 200 and optionally the clinician may identify the meningitis as chronic, thereby selecting the bacterial, viral, or fungal infection as represented by block 408, or optionally leaving the infection unidentified.

Following receipt of the etiology, a clinician may define the susceptibilities of the disease if etiology is organism specific. For example, different organisms may be resilient to different medical treatments. In the case of meningitis, the various rules may provide:

1. Antibiotic susceptibility list for GNRs (except *pseudomonas, Stenotrophomonas, acinetobacter, Hemophilus*), may include: Ampicillin/sulbactam, Cephalothin, Ceftazidime, Ceftriaxone, Cefotaxime, Ciprofloxacin, Gentamicin, Imipenem, Levofloxacin, Piperacillin, Piperacillin/tazobactam, Trimethoprim/sulfamethoxazole.
2. Antibiotic susceptibility list for *Pseudomonas* may include: Ceftazidime, Ciprofloxacin, Gentamicin, Imipenem, Piperacillin, Piperacillin/tazobactam.

3. Antibiotic susceptibility list for *Staphylococcus* may include: Oxacillin, Vancomycin, Rifampin.
4. Antibiotic susceptibility list for *Hemophilus* may include a $3^{rd}$ generation cephalosporin.
5. Similarly, antibiotic susceptibility list for *Neisseria meningitidis* may include a $3^{rd}$ generation cephalosporin.
6. Susceptibility for *Streptococcus pneumoniae* may include: Chloramphenicol, Vancomycin, and defined minimum inhibitory concentration (MIC) for pencillin, cefotaxime, ceftriaxone,
7. Susceptibility for *S. agalactiae* may include: Ampicillin and Gentamicin.

Upon defining any organism susceptibilities, the clinician may define one or more mitigating factors based upon etiology, as represented by blocks 410 and 412 in FIG. 20B. The mitigating factors may be specific to whether the organism is identified or whether the empiric therapy is to be used for an unknown organism. For example, for an identified organism the clinician may provide information related to abnormal kidney function, Antimicrobial resistance, current or recent treatment failure, and the like. Similarly, if the organism is unknown, the clinician may define information and data related to Abnormal kidney function, Recurrence/relapse, Age, HIV status, Alcoholism, Concurrent debilitating disease, Concurrent impaired cellular immunity, recent neurosurgery, recent head trauma, presence of V-P shunt, suspected MDR tuberculosis, and the like.

Following the data collection, system 200, and more specifically, decision-support module 210 generates a recommendation for treatment of the patient, by analyzing: (i) patient's drug allergies; (ii) patient's genetic variations with regard to drug metabolizing enzymes or genetic predisposition to diseases; (iii) genetic variations in the patient's ability to metabolize specific drugs; (iv) drug-drug interactions; (v) dosing requirements based on height, weight, age, sex, and the like; (vi) price; (vii) probability of success for curing the disease; (viii) monographs; (ix) antibiograms or antimicrobial-susceptibility patterns; and (x) formulae of the drug. Additionally, recommendations may include analyzing the need for a referral, additional tests, microbial susceptibility or genetic predisposition to the disease or medical condition, pharmacogenomic data, family history, behavioral and lifestyle changes, and patient education related to the medical condition or avoiding the medical condition. In this manner, system 200 may optionally evaluate the patient's long term risk for contracting or their predisposition or susceptibility to various medical conditions. Thus, decision-supported patient data or a decision supported progress note is created.

The above-recited process to generate the decision-supported patient data and the decision-supported progress note may use one or more statements and rules, as illustrated in FIGS. 21–24. Such statements and rules, stored in knowledge module 226, are used by inference module 232 to make the decision-supported recommendation for treatment of the medical condition. As illustrated, Table 13 contains a plurality of rules that are directed to the general decision-supporting process of determining a medical treatment for a medical condition of Meningitis. Tables 14–16 (FIGS. 22–24) contain a number of rules specific to certain information collected by system 200; specifically, optionally sequentially activated rules associated with the duration of treatment, mitigating factors, and caveats. The statements and rules contained in FIGS. 21–24 are specific to the diagnosis and treatment of Meningitis; however one skilled in the art may appreciate that various other rules may be appropriate.

The present invention may be embodied in other specific forms without departing from its spirit or essential characteristics. For example, embodiments of the present invention are also disclosed in copending U.S. patent application entitled "Systems and Methods for Communicating Between a Decision-Support System and One or More Mobile Information Devices", filed Sep. 21, 2000, which is incorporated herein in its entirety by reference. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. In a decision-support system having a decision-support module, having a knowledge base of medical conditions, diagnostic criteria, and treatments, that communicates with at least one client module adapted to aid with collecting patient data from a patient, a method for delivering decision-supported patient data to a clinician to aid the clinician with the diagnosis and treatment of a medical condition, the method comprising the steps of:

(a) at a client module remote from a decision-support module, presenting a patient with a plurality of questions generated by the decision-support module and gathering patient data indicative of a plurality of responses to the plurality of questions from the patient, wherein each question presented to the patient is based upon the prior questions presented to and the patient data gathered from the patient;

(b) upon receiving the patient data from the client module, evaluating the patient data at the decision-support module to generate decision-supported patient data, the decision-supported patient data comprising a medical condition diagnosis of the patient, pertinent medical parameters associated with the medical condition, and one or more medical care recommendations for the medical condition; and (c) at either the client module or another client module specific to the clinician, presenting the clinician with the decision-supported patient data specific to the patient in either a standardized format associated with a progress note or a format selected by the clinician that assists the clinician in treating the patient.

2. A method as recited in claim 1, further comprising the step of transmitting the decision-supported patient data to a user module.

3. A method as recited in claim 1, wherein the format of the decision-supported patient data is a decision-supported progress note.

4. A method as recited in claim 1, further comprising the step of tracking the success of the one or more medical care recommendations in treating the patient's medical condition identified through the decision-supported patient data.

5. A method as recited in claim 4, further comprising the step of delivering data indicating the success of the one or more medical care recommendations to a third party.

6. A method as recited in claim 1, further comprising the step of requesting patient data by querying one or more ancillary modules.

7. A method as recited in claim 1, further comprising the step of broadcasting the patient data to the clinician.

8. A method as recited in claim 7, wherein the step of broadcasting patient data comprises broadcasting patient data containing at least one alert to the clinician upon the occurrence of an alert event.

9. A method as recited in claim 7, wherein the step of broadcasting patient data comprises broadcasting patient data following a defined schedule.

10. A method as recited in claim 1, wherein the evaluating step comprises evaluating the patient data against patient data stored in a patient module.

11. A method as recited in claim 1, wherein the gathering step comprising the step of gathering patient data via a user interface, the user interface comprising at least one of a graphical user interface, an interactive user interface, a voice recognition user interface or a textual user interface.

12. A method as recited in claim 1, wherein the step of presenting the patient with a question comprises the steps of:
    (a) asking a question, of the plurality of questions, related to the patient's health;
    (b) following receiving at least one answer to the question and generating at least one additional question based upon the at least one answer, presenting the at least one additional question to the patient.

13. A method as recited in claim 1, wherein the format of the decision-supported patient data is either summarized decision-supported patient data or a decision-supported progress note.

14. A computer-readable medium having computer-executable instructions for performing the steps recited in claim 1.

15. A method as recited in claim 1, wherein the evaluating step comprises:
    (a) collecting medical condition information;
    (b) collecting a clinical classification of the medical condition;
    (c) collecting data representative of one or more causes of the medical condition;
    (d) collecting susceptibilities of the medical condition if the one or more causes of the medical condition is organism specific;
    (e) collecting mitigating factors based on the one or more causes of the medical condition; and
    (f) evaluating the medical condition, the clinical classification, the one or more causes, the susceptibilities, and the mitigating factors to generate decision-supported patient data.

16. A method as recited in claim 15, wherein the generating step comprising generating at least one additional question based upon the at least one answer and the data stored in the knowledge base.

17. A method as recited in claim 15, further comprising:
    (a) collecting a patient's genetic and/or environmental susceptibility to disease; and
    (b) collecting genetic variations of the patient to the patient's drug metabolizing enzymes.

18. A method as recited in claim 15, further comprising the step of collecting the patient's susceptibilities and predispositions for long term risk based upon the patient's family history and patient data associated with one or more relatives of the patient.

19. A method as recited in claim 15, further comprising the step of collecting patient data from genetic tests to evaluate the medical condition to generate the at least one medical recommendation.

20. A method as recited in claim 19, wherein at least one recommendation comprises at least one of (i) drug selection, (ii) drug duration, (iii) drug route, (iv) drug interval, (v) drug usage, and (vi) daily cost.

21. A method as recited in claim 15, further comprising the step of collecting patient data from pharmacogenomics data to generate at least one medical recommendation.

22. In a decision-support system having a decision-support module, having a knowledge base of medical conditions, diagnostic criteria, and treatments, that communicates with at least one client module adapted to aid with collecting patient data from a patient, a method for delivering a decision-supported progress note to a clinician to aid the clinician with the diagnosis and treatment of a medical condition, the method comprising the steps of:
    (a) upon delivering patient data to the decision-support module following a question/answer interaction between the patient and the client module, where the patient data is indicative of the responses to the question presented to the patient, evaluating the received patient data with the data stored in the knowledge base to generate data indicative of a decision-supported progress note having either a standardized format associated with a progress note or a format selected by the clinician that assists the clinician in treating the patient; and
    (b) delivering the data indicative of a decision-supported progress note to at least one client module to present at least one of the clinician and the patient with the decision-supported progress note in a format that assists the clinician in treating the patient.

23. A method as recited in claim 22, further comprising the step of transmitting the decision-supported progress note to a mobile client module.

24. A method as recited in claim 22, further comprising the step of displaying at least one referral to at least one another clinician in the decision-supported progress note.

25. A method as recited in claim 22, wherein the question/answer interaction comprises the steps of:
    (a) asking at least one question related to the patient's health;
    (b) receiving at least one answer to the at least one question;
    (c) generating at least one additional question based upon the at least one answer.

26. A method as recited in claim 22, further comprising a step of authorizing at least one medical care recommendation based upon the decision-supported progress note.

27. A method as recited in claim 26, further comprising a step of generating at least one billing code and at least one authorization documentation for at least one medical care recommendation associated with the decision-supported progress note.

28. A method as recited in claim 22, further comprising collecting at least one of (i) genetic data and family history from the patient and (ii) pharmacogenomic data related to the patient.

29. A method as recited in claim 22, further comprising a step of using one or more rules to generate decision-supported patient data, associated with the decision-supported progress note, based upon the patient data stored at the decision-support module and patient data newly gathered from the client module.

30. A method as recited in claim 22, further comprising a step of authorizing at least one referral based upon evaluating the patient data.

31. A method as recited in claim 30, further comprising the step of delivering the at least one referral to a third party insurance provider.

32. A method as recited in claim 22, wherein the step of delivering comprises delivering the decision-supported progress note to at least one of: (i) a mobile information device; (ii) a third party; and (iii) a clinician's assistant.

33. A method as recited in claim 32, wherein the decision-supported progress note comprises at least one of: (i) a medical condition diagnosis; (ii) at least one medical care recommendation; and (iii) at least one alert.

34. A computer-readable medium having computer-executable instructions for performing the steps recited in claim 22.

35. In a decision-support system having a decision-support module, having a knowledge base of medical conditions, diagnostic criteria, and treatments, that communicates with at least one client module, a method for delivering decision-supported patient data to a clinician to aid the clinician with the diagnosis and treatment of a medical condition, the method comprising the steps of:

(a) receiving patient data from the at least one client module remote from the decision-support module, the patient data being gathered from a patient in response to a decision-supported questionnaire generated by the decision-support module based upon questions presented to the patient, responses to the presented questions, and the knowledge base;

(b) evaluating the patient data with the knowledge base of the decision-support module to generate decision-supported patient data for the patient, the decision-supported patient data comprising a medical condition diagnosis of the patient, pertinent medical parameters associated with the medical condition, and one or more medical care recommendations; and (c) delivering the decision-supported patient data to a user module for presenting the clinician with the decision-supported patient data specific to the patient in either a standardized format associated with a progress note or a format selected by the clinician that assists the clinician in treating the patient.

36. A decision-support system, comprising:

(a) a decision-support module configured to generate decision-supported patient data specific to each patient that a clinician is to examine in a defined period, the decision-support module comprising:

(i) a knowledge module storing data representative of expert knowledge within at least one medical field;

(ii) a patient module configured to store patient data; and (iii) an inference module communicating with the knowledge module and the patient module, the inference module being configured to generate a decision-supported progress note; and (b) a client module in communication with the decision-support module and adapted to present the decision-supported progress note to the clinician in a configuration that assists the clinician in treating each patient.

* * * * *